United States Patent
Forsell

(10) Patent No.: US 7,338,437 B2
(45) Date of Patent: *Mar. 4, 2008

(54) MALE SEXUAL IMPOTENCE TREATMENT APPARATUS

(75) Inventor: Peter Forsell, Zug (SE)

(73) Assignee: Obtech Medical AG, Baar (CH)

( * ) Notice: Subject to any disclaimer, the term of this patent is extended or adjusted under 35 U.S.C. 154(b) by 738 days.

This patent is subject to a terminal disclaimer.

(21) Appl. No.: 10/203,432

(22) PCT Filed: Feb. 14, 2001

(86) PCT No.: PCT/SE01/00305

§ 371 (c)(1),
(2), (4) Date: Nov. 25, 2002

(87) PCT Pub. No.: WO01/54626

PCT Pub. Date: Aug. 2, 2001

(65) Prior Publication Data

US 2003/0135089 A1    Jul. 17, 2003

Related U.S. Application Data

(60) Provisional application No. 60/182,221, filed on Feb. 14, 2000.

(51) Int. Cl.
*A61F 5/00* (2006.01)

(52) U.S. Cl. ........................................................ 600/38

(58) Field of Classification Search ............ 600/38–41, 600/29–32; 128/DIG. 25, 897–899; 606/151–158, 606/201–203

See application file for complete search history.

(56) References Cited

U.S. PATENT DOCUMENTS

| | | |
|---|---|---|
| 4,829,990 A | 5/1989 | Thuroff et al. |
| 4,982,731 A | 1/1991 | Lue et al. |
| 5,509,888 A | 4/1996 | Miller |

OTHER PUBLICATIONS

International Search Report for International Application No. PCT/SE01/00305.

*Primary Examiner*—John P. Lacyk
(74) *Attorney, Agent, or Firm*—Nixon & Vanderhye P.C.

(57) ABSTRACT

A male sexual impotence treatment apparatus comprises an adjustable restriction device (234) implanted in an impotent patient and engaging the corpora cavernosa or crura or the prolongation thereof (244). An implanted adjustment device is adapted to adjust the restriction device to temporarily contract the corpora cavernosa, in order to restrict the blood flow leaving the penis when the patient desires to achieve erection. An implanted powered hydraulic operation device (246) operates the adjustment device.

174 Claims, 9 Drawing Sheets

NO FLOW

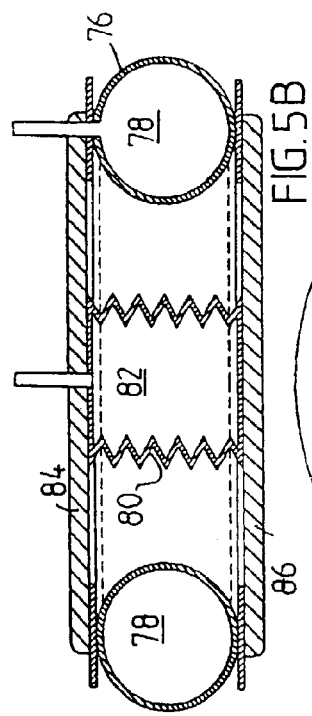
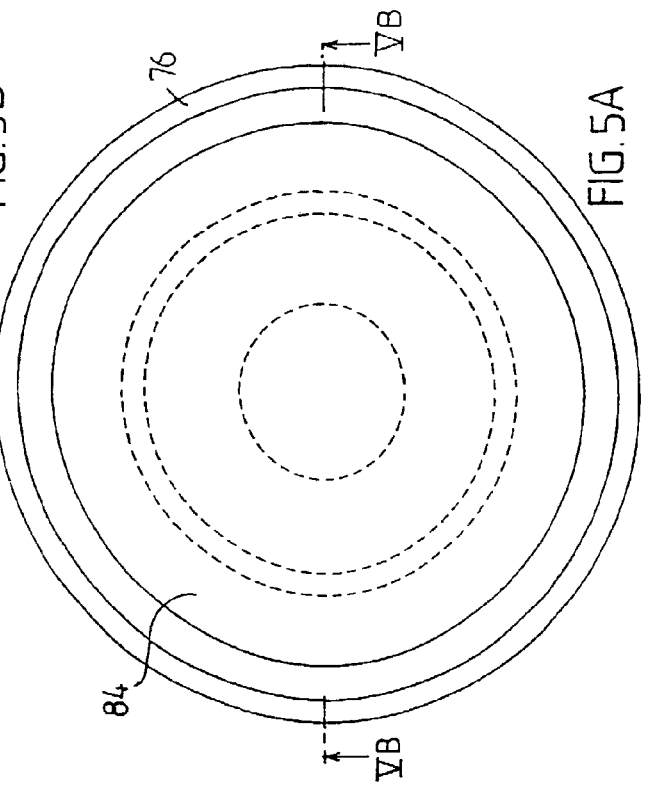
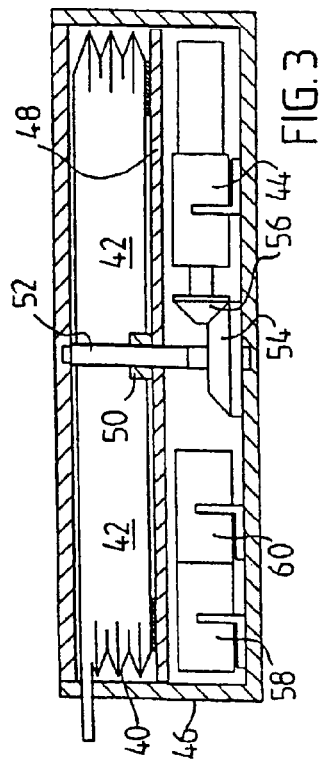
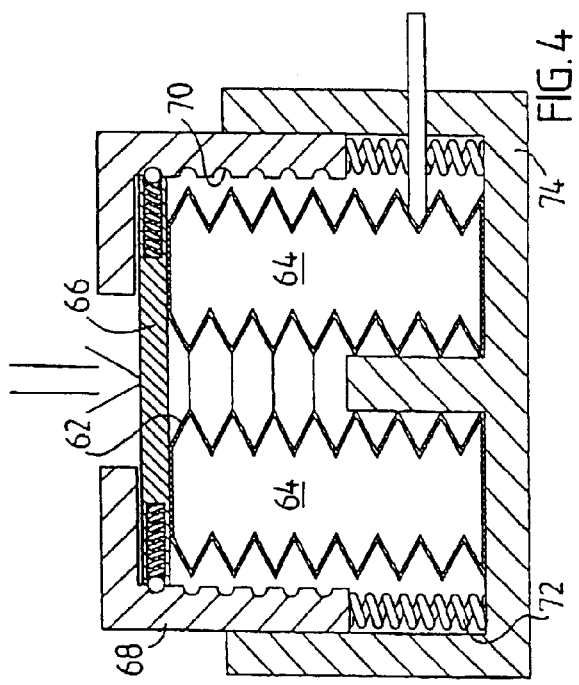

MALE SEXUAL IMPOTENCE TREATMENT APPARATUS

This application is the U.S. National Phase of International Application No. PCT/SE01/00305, filed Feb. 14, 2001, which designated the U.S., and which claims the benefit of Provisional Application Ser. No. 60/182,221, filed Feb. 14, 2000.

The present invention relates to a male sexual impotence treatment apparatus comprising an adjustable restriction device implantable in a male impotent patient for engaging the corpora cavernosa or crura or the prolongations thereof of the patient's penile tissue. An implantable adjustment device is provided for adjusting the restriction device to temporarily contract the corpora cavernosa or crura or the prolongations thereof to restrict the blood flow leaving the penis, and an implantable operation device is provided for operating the adjustment device.

Male sexual impotence is a widespread problem. Many different solutions to this problem have been tried. A main solution currently practised and disclosed in for instance U.S. Pat. Nos. 5,437,605 and 4,841,461 is to implant a hydraulic inflatable/contractable silicon prosthesis in the cavities of the corpora cavernosa of the patient's penis. In fluid connection with this prosthesis is a reservoir implanted in the scrotum. By manual pumping action the prosthesis is filled with fluid from the reservoir to effect errect penile condition or is emptied of fluid, which returns to the reservoir, to effect flaccid penile condition. However, there are several more or less severe disadvantages of this main solution. Above all, the penis is more or less damaged by the operation and it is practically impossible to reverse the operation. Another disadvantage is that rather strong forces act against this implanted prosthesis resulting in a significant risk of the prosthesis being broken.

Another solution to achieve erection is to restrict the blood flow leaving the penis. For example, U.S. Pat. No. 4,829,990 discloses two hydraulically operated inflatable cuffs wrapped around the respective crura. A disadvantage of such a solution is that it involves complicated surgery. Another example on this solution is U.S. Pat. No. 4,828,544, which discloses an artificial fistula system surgically implanted and providing a primary fistula between the femoral artery and the femoral vein and a secondary fistula for leading blood from the the primary fistula to the penis. An inflatable balloon engages the primary fistula between the secondary fistula and the vein. The balloon is in fluid connection with a manually compressible reservoir implanted in the scrotum. Again, implantation of this artifical fistula system requires delicate surgery.

Yet another solution is to inject a substance in the penile vein system to achieve erection. However, injections are painful and complicated for the patient.

The object of the present invention is to provide a simple male sexual impotence treatment apparatus, which requires relatively uncomplicated surgery.

This objekt is obtained by an apparatus of the kind described initially characterised in that the operation device comprises a powered operation device.

With the expression "the prolongations thereof" should be understood the penile tissue extending from the crura inside the human body and following the pathway of the blood flow leaving the penis, i.e. where the penile exit veins extend.

Generally, the restriction device is adapted to contract the corpora cavernosa or crura or the prolongations thereof as a single unit, which requires relatively simple surgery. Alternatively, however, the restriction device may comprise two restriction members adapted to contract the respective corpora cavernosa or crura or the prolongations thereof.

The restriction device may control the contraction of the corpora cavernosa or crura or the prolongations thereof, preferably to change steplessly. Suitably, the adjustment device adjusts the restriction device such that the restriction device provides a predetermined contraction of the corpora cavernosa or crura or the prolongations thereof that is satisfactory for the patient. A satisfactory contraction is achieved when the differential pressure between the arterial and venous penile blood pressures has increased enough to cause erection of the patient's penis while blood still is flowing through the penis.

The adjustment device preferably adjusts the restriction device in a non-invasive manner.

The adjustment device may adjust the restriction device in a non-magnetic manner, i.e. magnetic forces may not be involved when adjusting the restriction device. Also, the adjustment device may adjust the restriction device in a non-thermal manner, i.e. thermal energy may not be involved when adjusting the restriction device.

The expression "powered" should be understood as energised with everything without manual force, preferably electric energy. In other words, the adjustment device is operated in a non-manual manner. The expression "non-manual manner" should be understood to mean that the adjustment device is not operated by manually touching subcutaneously implanted components of the apparatus or not manipulated by touching the skin of the patient. Thus, as opposed to prior practice when treating male sexual impotence, the adjustment device of the invention is not operated by manual forces, such as by manually compressing a fluid containing balloon implanted in the scrotum or in the region of labia majora. Of course, manual manipulation of a subcutaneous start button or the like for activating the powered operation device is permitted within the scope of the present invention.

Alternatively, or in combination with a powered operation device, the servo means may be used, which enables manual manipulation without need for strong manipulation forces. The servo means may comprise hydraulic means, electric control means, magnetic means, or mechanical means, which may be activated by manual manipulating means. Using a servo system will save the use of force when adjusting the adjustment device, which may be of importance in many applications.

The term "servo means" encompasses the normal definition of a servo mechanism, i.e. an automatic device that controls large amounts of power by means of very small amounts of power, but may alternatively or additionally encompass the definition of a mechanism that transfers a weak force acting on a moving element having a long stroke into a strong force acting on another moving element having a short stroke. The servo means may comprise a motor, preferably an electric motor, which may be reversible.

In accordance with a main embodiment of the invention, the apparatus comprises a reservoir, preferably containing a predetermined amount of hydraulic fluid, also implantable in the patient, wherein the operation device, suitably electrically powered, operates the adjustment device by using the hydraulic fluid of the reservoir.

The adjustment device may comprise an expandable cavity in the restriction device, wherein the corpus cavernosum or crura or the prolongation thereof is sqeezed upon expansion of the cavity and released upon contraction of the cavity. In this embodiment the operation device is adapted to distribute hydraulic fluid from the reservoir to expand the cavity, and from the cavity to the reservoir to contract the cavity.

A fluid distribution tube may readily be connected between the reservoir and the cavity in a manner so that the tube does not interfere with other implanted components of the apparatus.

Preferably, the reservoir defines a chamber for the predetermined amount of fluid and the operation device changes the volume of the chamber. The operation device suitably comprises first and second wall portions of the reservoir and is adapted to provide relative displacement between the first and second wall portions of the reservoir, in order to change the volume of the chamber.

The operation device may be adapted to provide said relative displacement in response to the pressure in the reservoir. Suitably, the operation device comprises a pressure controlled hydraulic operation device. For safety, an alarm may be provided for generating an alarm signal in response to the lapse of a predetermined time period during which the pressure controlling the hydraulic operation device exceeds a predetermined high value.

Suitably, the operation device is adapted to distribute fluid from the reservoir to the cavity of the restriction member in response to a predetermined first displacement of the first wall portion of the reservoir relative to the second wall portion of the reservoir and may distribute fluid from the cavity to the reservoir in response to a predetermined second displacement of the first wall portion relative to the second wall portion.

The first and second wall portions of the reservoir may be displaceable relative to each other by a magnetic, hydraulic, or electric power means, such as an electric motor. In this embodiment no pump is used, only the volume of the reservoir is varied. This is of great advantage compared to the solution described below when the operation device comprises a pump used to pump fluid between the reservoir and the adjustment device because there is no need for a non-return valve and it is still possible to have fluid going both to and from the reservoir. Thus, the significant risk of malfunction when using such a non-return valve implanted in the patient is eliminated.

The operation device may comprise hydraulic means and a fluid conduit extending between the hydraulic means and the adjustment device. The hydraulic means and conduit are devoid of any non-return valve. The reservoir may form part of the conduit and a fluid chamber with a variable volume. The operation device may distribute fluid from the fluid chamber to the adjustment device by reduction of the volume of the chamber and withdraw fluid from the adjustment device by expansion of the volume of the chamber. The operation device preferably comprises a motor for moving a movable wall of the reservoir for changing the volume of the chamber. Any kind of motor could be used for the different operations as well as wireless remote solutions for controlling the operations.

The restriction device preferably is operable to perform a reversible function and accordingly there is a reversing device implantable in the patient for reversing the function performed by the restriction device. Such a reversing function preferably involves enlarging and restricting the blood flow passageway by the restriction device, suitably in a stepless manner. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a gearbox.

Where the reversing device comprises a switch the control device suitably controls the operation of the switch by shifting polarity of released energy supplied to the switch. The switch may comprise an electric switch and the source of energy may supply electric energy for the operation of the switch. The switch mentioned above may comprise an electronic switch or, where applicable, a mechanical switch.

Where the operation device comprises a motor, the reversing device is adapted to reverse the motor.

In accordance with another particular embodiment of the invention, the operation device comprises a pump for pumping fluid between the reservoir and the adjustment device. A mechanical solution is proposed in which it is possible to pump fluid from the reservoir to the adjustment device and vice versa just by pushing an activation member in one direction. The pump preferably comprises a first activation member for activating the pump to pump fluid from the reservoir to the adjustment device, and a second activation member for activating the pump to pump fluid from the adjustment device to the reservoir. At least one of the first and second activation members may be operable by manual manipulation, preferably to permit manual pushing, pulling or rotation thereof in one direction, or by a device powered magnetically, hydraulically, or electrically (e.g. by an electric motor), or be operable by a combination of these methods. Suitably, at least one of the activation members may be adapted to operate when subjected to an external pressure exceeding a predtermined magnitude.

Another alternative is a pump pumping in only one direction and an adjustable valve to change the direction of fluid to either increase or decrease the amount of fluid in the reservoir. This valve may be manipulated either manually, mechanically, magnetically, or hydraulically.

The main embodiment of the invention described above including the reservoir may alternatively be equipped with a servo means comprising a reverse servo. The term "reverse servo" is to be understood as a mechanism that transfers a strong force acting on a moving element having a short stroke into a weak force acting on another moving element having a long stroke; i.e. the reverse function of the above-defined alternative mechanism of a normal servo mechanism. A first closed hydraulic system that controls another closed hydraulic system in which hydraulic means of the adjustment device is incorporated may be used. Minor changes in the amount of fluid in a smaller reservoir of the first system could then be transferred by the reverse servo into major changes in the amount of fluid in a larger reservoir in the second system. In consequence, the change of volume in the larger reservoir of the second system affects the hydraulic means of the adjustment device. For example, a short stroke that decreases the volume of the smaller reservoir will cause the larger reservoir to supply the adjustment device with a large amount of hydraulic fluid, which in turn results in a long mechanical adjustment stroke on the restriction device.

The great advantage of using such a reverse servo is that the larger volume system could be placed inside the abdomen or retroperitoneum where there is more space and still it would be possible to use manual manipulation means of the smaller system subcutaneously. The smaller reservoir could be controlled directly or indirectly by a fluid supply means. The fluid supply means may include another small reservoir, which may be placed subcutaneously and may be activated by manual manipulation means. Both the normal servo means and the specific reverse servo may be used in connection with all of the various components and solutions described in the present specification.

Thus, the reverse servo may be adapted to provide relative displacement between the first and second wall portions of the reservoir, suitably in response to the pressure in the reservoir, in order to change the volume of the chamber of the reservoir.

Generally, the servo means, including the reverse servo, comprises a pressure controlled servo means. The alarm mentioned above may alternatively be adapted to generate an alarm signal in response to the lapse of a predetermined time period during which the pressure controlling the servo means exceeds a predetermined high value.

The reverse servo may comprise magnetic means, electric means or manual manipulation means or a combination thereof. Preferably, however, the reverse servo comprises hydraulic means.

In accordance with a particular embodiment of the invention, the reverse servo further comprises a servo reservoir defining a chamber containing servo fluid, and the operation device comprise first and second wall portions of the servo reservoir, which are displaceable relative to each other to change the volume of the chamber of the servo reservoir. The first and second wall portions of the servo reservoir may be displaceable relative to each other by magnetic means, hydraulic means, or electric control means.

Where the reverse servo comprises hydraulic means it may further comprise a fluid supply reservoir connected to the servo reservoir in a closed system and containing a further predetermined amount of fluid. The fluid supply reservoir defines a chamber for the further predetermined amount of fluid and the operation device is adapted to change the volume of the chamber and thereby control the amount of fluid in the servo reservoir. The fluid supply reservoir comprises first and second wall portions, which are displaceable relative to each other to change the volume of the chamber of the fluid supply reservoir. Suitably, the fluid supply reservoir increases the amount of fluid in the servo reservoir in response to a predetermined first displacement of the first wall portion of the fluid supply reservoir relative to the second wall portion of the fluid supply reservoir and decreases the amount of fluid in the servo reservoir in response to a predetermined second displacement of the first wall portion of the fluid supply reservoir relative to the second wall portion of the fluid supply reservoir.

In accordance with an embodiment of the invention, the adjustment device comprises a hydraulic adjustment device, and an implantable reservoir containing a predetermined amount of hydraulic fluid and a conduit providing fluid connection between the reservoir and the hydraulic adjustment device are provided. The operation device is adapted to operate the hydraulic adjustment device by distributing hydraulic fluid through the conduit between the reservoir and the hydraulic adjustment device, wherein the conduit and hydraulic adjustment device are devoid of any non-return valve to permit free flow of hydraulic fluid in both directions in the conduit. Preferably, the reservoir forms a fluid chamber with a variable volume, and the operation device is adapted to distribute fluid from the chamber to the adjustment device by reduction of the volume of the chamber and to withdraw fluid from the adjustment device by expansion of the volume of the chamber. The operation device may comprise a motor or a pump. Alternatively, the operation device may comprise a movable wall of the reservoir for changing the volume of the chamber. For example, the operation device may be adapted to change the volume of the chamber by moving the movable wall in response to the pressure in the chamber.

In the above embodiments including a reservoir for hydraulic fluid an injection port may be provided for subcutaneous implantation in the patient to be in fluid communication with the chamber of the reservoir. The injection port may be integrated in the reservoir. Such an injection port may be provided for enabling, normally single, once-and-for-all, calibration of the amount of fluid in the hydraulic system used.

In the various embodiments hereinafter described the restriction device generally forms an at least substantially closed loop. However, the restriction device may take a variety of different shapes, such as the shape of a square, rectangle or ellipse. The substantially closed loop could for example be totally flat, i.e. thin as seen in the radial direction. The shape of restriction device may also be changed during use, by rotation or movements of the restriction device in any direction. A physical lumen, such as the corpora cavernosa or crura, often is easier to contract by moving two opposite sidewalls of the lumen against each other. Thus, the restriction device may be designed to perform such a contracting effect of the opposite walls of the corpora cavernosa or crura or the prolongations thereof, or alternatively the opposite walls of each one of the corpora cavernosa or crura or the prolongations thereof. Either mechanical or hydraulic solutions may be employed to operate the restriction device. Alternatively, the restriction device may comprise an adjustable cuff, a clamp or a roller for bending or rotating the corpora cavernosa or crura or the prolongations thereof to contract them. The bending or rotating members may take any shape and be either hydraulic or non-inflatable.

Preferably the restriction device comprises an elongated restriction member and forming means for forming the restriction member into at least a substantially closed loop around the corpora cavernosa or crura or the prolongations thereof, wherein the loop defines a restriction opening, whereby the adjustment device adjusts the restriction member in the loop to restrict the blood flow leaving the penis.

Advantageously, the forming means may form the restriction member into a loop having a predetermined size. Alternatively, the forming means may form the restriction member into a loop selected from several predetermined sizes.

The adjustment device may change the size of the restriction opening such that the outer circumferential confinement surface of the restriction member either is changed or is unchanged.

The elongated restriction member may be flexible, for example take the shape of a belt or cord, and the adjustment device may pull a first portion of the flexible restriction member from a second portion of the flexible restriction member opposite the first portion in the loop to squeeze the corpora cavernosa or crura or the prolongations thereof between the opposite lengths of the elongated flexible restriction member to restrict the blood flow leaving the penis. The restriction member may be non-inflatable, and the adjustment device may mechanically adjust the restriction member in the loop.

Preferably the adjustment device is operable to adjust the restriction device to steplessly change the contraction of the corpora cavernosa or crura or the prolongations thereof.

The adjustment device may mechanically or hydraulically adjust the restriction device. In the embodiments described the adjustment device may either mechanically or hydraulically adjust the restriction device, where applicable. It should be noted that the operation device might mechanically or hydraulically operate the adjustment device irrespectively of whether the adjustment device is adapted to adjust the restriction device mechanically or hydraulically.

In accordance with an embodiment of the invention, the restriction device comprises at least two elements on opposite or different sides of the corpus cavernosum or crura or the prolongation thereof, and the adjustment device decreases the distance between the elements to squeeze the corpus cavernosum or crura or the prolongation thereof between the elements, thereby restricting the blood flow passageway. It is also possible to use only one element and squeeze the corpus cavernosum or crura or the prolongation thereof against human bone or tissue. The elements above may as well as all the restriction members mentioned in this application be everything from rigid to soft.

In accordance with an alternative, the restriction device bends or rotates a portion of the corpus cavernosum or crura or the prolongation thereof to restrict the blood flow passageway in the same. For example, the restriction device may comprise at least two bending members, such as cylindrical or hour-glass shaped rollers, positioned on opposite or different sides of the corpus cavernosum or crura or the prolongation thereof and displaced relative to each other along the corpus cavernosum or crura or the prolongation thereof, and the adjustment device may move the bending members against the corpus cavernosum or crura or the prolongation thereof to bend the latter to restrict the blood flow passageway. The restriction device may also rotate a portion of the corpus cavernosum or crura or the prolongation thereof. The bending or rotating members may take any shape and be either hydraulic or non-inflatable.

Alternatively, the two bending members one placed more distal than the other may be rotated in opposite directions relative to each other. With interconnecting means for example flexible bands between the bending members a restriction will occur between the bending members when they are rotated.

Preferably the adjustment device is operable to adjust the restriction device to steplessly change the restriction of the blood flow passageway in the corpus cavernosum or crura or the prolongation thereof.

All embodiments according to the invention may be controlled by a wireless remote control.

In accordance with an advantageous embodiment of the invention, there is provided a wireless remote control for non-invasively controlling the operation device. The remote control may conveniently comprise an external hand-held remote control unit, which is manually operable by the patient to control the restriction device to squeeze and release the corpus cavernosum or crura or the prolongation thereof. With the wireless remote control the apparatus of the invention is conveniently controlled by the patient when he so desires, which is of great advantage compared to the prior art procedures. With the remote control the apparatus of the invention is conveniently controlled to adjust the implanted restriction device to release the blood flow passageway when the patient wants to relieve himself or herself.

The remote control may advantageously be capable of obtaining information related to important parameters, such as the condition of the blood flow passageway or the pressure against the restriction device, and of commanding the operation device to operate the adjustment device to adjust the restriction device in response to obtained information. With the remote control the apparatus of the invention is conveniently controlled to adjust the implanted restriction device to open and close the blood flow passageway. The adjustment device may control the restriction device to steplessly change the restriction of the passageway.

Preferably, the wireless remote control comprises a separate signal transmitter or receiver and a signal receiver or transmitter implanted in the patient. For example, the signal transmitter and signal receiver may transmit and receive a signal in the form of digital pulses, which may comprise a magnetic or electric field. Alternatively, which is preferred, the signal transmitter and signal receiver may transmit and receive an electromagnetic wave signal, a sound wave signal or a carrier wave signal for a remote control signal. The receiver may comprise an implanted control unit for controlling the adjustment device in response to a control signal from the signal transmitter. Any known or conventional signal transmitting or signal receiving means that is suitable for use with a human or mammal patient may be provided as the signal transmitter or signal receiver.

The apparatus of the invention may further comprise an implanted energiser unit for providing energy to energy consuming implanted components of the apparatus, such as electronic circuits and/or a motor for operating the adjustment device. Where a motor is provided the control unit is adapted to power the motor with energy provided by the energiser unit in response to a control signal received from the signal transmitter. The motor may be any type of motor, such as a pneumatic, hydraulic or electric motor and the energiser unit may power the motor with pressurized gas or liquid, or electric energy, depending on the type of motor. Where the motor is an electric motor, it may power pneumatic or hydraulic equipment.

The remote control advantageously comprises wireless energy transfer device for transferring energy from outside the patient's body to energy consuming implantable components of the apparatus. The energy transfer device may comprise said energiser unit is adapted to transform energy from the control signal, as it is transmitted to the signal receiver, into electric energy. Where the operation device comprises a motor the wireless energy transfer device is adapted to directly power the motor with transferred energy.

The energy transferred by the wireless energy transfer device preferably comprises a signal, suitably a wave signal. The energy transferred by the wireless energy transfer device may comprise an electric field or a magnetic field or a combination thereof. The signal may be analog or digital or a combination thereof. The energy transfer device may transfer the energy from the signal into a direct, pulsating direct or alternating current or a combination thereof.

Any of the above mentioned signals may comprise analog or digital pulses. The analog or digital signal may comprise a magnetic field or an electric field or a combination thereof. Where the signal is a wave signal it may comprise an electromagnetic wave signal, a sound wave signal or a carrier wave signal for a remote control signal or a combination thereof. Where a carrier signal is used it may be frequency, amplitude or frequency and amplitude modulated.

The apparatus of the invention may comprise an implantable source of energy for powering the operation device and/or for energizing other energy consuming components of the apparatus, wherein the energy from the source of energy is releasable from outside the patient's body. Furthermore, the apparatus may comprise an energy transmission device for wireless transmission of energy of a first form and an energy transforming device implantable in the patient for transforming the energy of the first form into energy of a second form, to be supplied to the source of energy and/or other implantable energy consuming parts of the apparatus. The energy transforming device may transform the wireless energy directly or indirectly into energy different than the wireless energy for operation of the restriction device. Typically, the energy of the second form is different than the energy of the first form. The function of the energy transmission device may be different from that of the energy transforming device.

An implantable motor or pump for operating the adjustment device may be provided, wherein the energy transmission device may be adapted to transmit wireless energy in the form of a magnetic field or electromagnetic waves or field for direct power of the motor or pump, as the wireless energy is being transmitted. Suitably, the energy transmission device transmits energy by at least one signal separate from the above mentioned control signal.

An implantable stabiliser for stabilising the energy of the first or second form may be provided. Where the energy of the second form comprises electric current, the stabiliser suitably comprises at least one capacitor.

Generally, the source of energy comprises a battery, accumulator, capacitor or a combination thereof.

In accordance with an embodiment of the invention, the apparatus comprises a control device adapted to produce wireless energy for directly powering the operation device and/or for energizing other energy consuming components of the apparatus.

Generally, the wireless energy may comprise a wave signal including a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Any of the above mentioned signals may comprise a wave signal including a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

The control device may be adapted to produce wireless energy in the form of a train of energy pulses and the energy transfer device may be adapted to intermittently transfer the train of energy pulses for direct use in connection with the energising of the energy consuming components of the apparatus. Alternatively, the control device may be adapted to control the energy transforming device to produce the energy of the second form in said train of energy pulses for direct use in connection with the operation of the adjustment device. The transferred energy preferably comprises electric energy. An implantable capacitor may be provided for producing the train of energy pulses.

Where a capacitor is used in any of the above described embodiments it may have a relatively low capacity, i.e. less than 0,1 μF, in order to be small and suited for implantation.

Where the operation device comprises an implantable motor or pump for operating the adjustment device, the energy transfer device may be adapted to directly power the motor or pump with transferred energy, at the same time as the energy is transferred. Where a pump is used it should not be a plunger type of pump, because a plunger pump is noisy, but may comprise a peristaltic or membrane pump.

As mentioned above the apparatus comprises a wireless remote control for non-invasively controlling the operation device, which preferably is electrically powered. Alternatively, the operation device is powered by magnetic energy, non-magnetic energy, electromagnetic energy, non-electromagnetic energy, kinetic energy, non-kinetic energy, sonic energy, non-sonic energy, thermal energy or non-thermal energy. However, the operation device may be unpowerable by permanent static magnetic energy. Any other kind of energy, such as electric, electromagnetic energy or a moving permanent magnetic energy, may be conceivable for operating the adjustment device. As a result, the implanted restriction device would not be accidentally adjusted if the patient comes close to any permanent magnet. Suitably, the operation device is adapted to non-invasively operate the adjustment device.

Where the operation device comprises a hydraulic operation device it may use hydraulic fluid, the viscosity of which changes when the hydraulic fluid is exposed to energy, preferably electric energy, different than thermal energy. However, use of hydraulic fluid of the kind having a viscosity that substantially increases when exposed to heat or a magnetic field, i.e. the hydraulic fluid would not become more viscous when exposed to heat or influenced by magnetic forces, should be avoided, because external heat sources or heat from the body when the patient has fever and external magnetic sources might affect the implanted components of the apparatus.

The adjustment device is may be operable to adjust the restriction device to steplessly change the restriction of the blood flow passageway. Furthermore, the adjustment device may be adapted to mechanically adjust the restriction device. Alternatively, it may be adapted to hydraulically adjust the restriction device by using hydraulic means, which is devoid of hydraulic fluid of the kind having a viscosity that substantially increases when exposed to heat or a magnetic field.

In accordance with an embodiment of the invention, the apparatus comprises a control device for controlling the restriction device. The control device may comprise an internal programmable control unit implantable in the patient and, possibly an external control unit outside the patient's body for programming the programmable internal control unit. Alternatively, the external control unit may be programmable and wirelessly control the restriction device. The control device may be adapted to produce wireless energy for directly powering the operation device and/or for energizing other energy consuming components of the apparatus.

At least one sensor for sensing at least one physical parameter of the patient may conveniently be implanted in the patient. The sensor may preferably sense as the physical parameter ejaculation, for example by sensing the pressure or flow in the patient's urethra, and either the internal control unit or the external control unit of the control device may suitably control the restriction device to release the corpora cavernosa or crura or the prolongations thereof in response to the sensor sensing ejaculation. For safety the restriction device may release the corpora cavernosa or crura or the prolongations thereof in response to the sensor sensing for example an abnormally high pressure value. The internal control unit may directly control the restriction device in response to signals from the sensor.

The pressure sensor may be any suitable known or conventional pressure sensor such as shown in U.S. Pat. Nos. 5,540,731, 4,846,181, 4738267, 4571749, 4407296 or 3939823; or an NPC-102 Medical Angioplasty Sensor.

Either the internal control unit or the external control unit of the control device may suitably control the restriction device to enlarge or close the blood flow passageway. For safety the restriction device may enlarge or open the blood flow passageway in response to the sensor sensing for example an abnormally high pressure value. The internal control unit may directly control the restriction device in response to signals from the sensor.

Wherever magnetic means is utilized according to the invention it may comprise a permanent magnet and a magnetic material reed switch, or other suitable known or conventional magnetic means.

Where a source of energy is used the control device suitably is operable from outside the patient's body for controlling the source of energy to release energy for use in connection with the operation of the adjustment device, when the adjustment device is implanted. The source of energy may be provided external to the patient's body, and the control device may be adapted to control the external source of energy to release wireless energy for use in connection with the operation of the adjustment device.

The control device may control the source of energy to release magnetic energy, non-magnetic energy, electromagnetic energy, non-electromagnetic energy, kinetic energy, non-kinetic energy, sonic energy, non-sonic energy, thermal energy or non-thermal energy, preferably in a non-invasive manner and for a determined time period and/or in a determined number of energy pulses.

Where the implantable components of the apparatus comprise electrical components they may include at least one or a single voltage level guard. In this case, the electrical components suitably are devoid of any current detector and/or charge level detector. Furthermore, the electrical components may comprise a capacitor or accumulator, wherein the charge and discharge of the capacitor or accumulator is controlled by use of the voltage level guard. As a result, there is no need for any implanted current detector and/or charge level detector for the control of the capacitor, which makes the apparatus simple and reliable.

In accordance with an advantageous embodiment of the invention, the apparatus comprises an implantable switch for directly or indirectly switching the operation of the restriction device. The switch may be operated by the energy supplied by the energy transmission device mentioned above to switch from an off mode, in which the implantable source of energy mentioned above is not in use, to an on mode, in which the source of energy supplies energy for the operation of the restriction device.

In accordance with an alternative embodiment, the above mentioned a remote control may be employed for controlling the implantable source of energy, wherein the switch is operated by the energy supplied by the energy transmission device to switch from an off mode, in which the remote control is prevented from controlling the source of energy and the source of energy is not in use, to a standby mode, in which the remote control is permitted to control the source of energy to supply energy for the operation of the restriction device.

In accordance with another alternative embodiment, the switch is operated by the energy supplied by the implantable energy transforming device mentioned above to switch from an off mode, in which the source of energy is not in use, to an on mode, in which the source of energy supplies energy for the operation of the restriction device.

In accordance with yet another alternative embodiment, the switch is operated by the energy supplied by the energy transforming device to switch from an off mode, in which the remote control is prevented from controlling the source of energy and the source of energy is not in use, to a standby mode, in which the remote control is permitted to control the source of energy to supply energy for the operation of the restriction device.

Suitably, the restriction device is embedded in a soft or gel-like material, such as a silicone material having hardness less than 20 Shore.

The energy transforming device may be designed to be implanted subcutaneously or in the abdomen, thorax or cephalic region of the patient.

The adjustment device may be adapted to adjust the restriction device such that the restriction device provides a predetermined contraction of the blood flow passageway that is satisfactory for the patient.

All the above described various components, such as the motor, pump and capacitor, may be combined in the different embodiments where applicable. Also the various functions described in connection with the above embodiments of the invention may be used in different applications, where applicable. Specifically, the various remote control functions described and all the various methods for supplying energy may be used in any conceivable combination that is apparent to those skilled in the art.

The invention also provides a method for treating male sexual impotence, comprising surgically implanting in the body of a male impotent patient an adjustable restriction device engaging the corpora cavernosa or crura or the prolongations thereof as a single unit, and when desired to achieve erection, adjusting the restriction device to temporarily contract the corpora cavernosa or crura or the prolongations thereof to restrict the blood flow leaving the penis.

The invention also provides another method for treating male sexual impotence, comprising surgically implanting in the body of a male impotent patient at least two adjustable restriction devices engaging the respective corpora cavernosa or crura or the prolongations thereof as separate units of the patients penis, and when desired to achieve erection, non-manually without touching the skin of the patient adjusting the restriction devices to temporarily contract the corpora cavernosa or crura or the prolongations thereof to restrict the blood flow leaving the penis. The method may further comprise surgically implanting one or more non-manually adjustble powered restriction devices engaging respective exit veins from the penis.

The method may further comprise implanting a source of energy in the patient and providing a control device for controlling the source of energy from outside the patient's body to supply energy to the restriction device or alternatively energising energy consuming components of the apparatus with wirelessly transmitted energy from outside the patient's body.

The invention also provides a laparoscopic surgical method. Thus, there is provided a method comprising the steps of placing at least two laparoscopical trocars in a male impotent patient's body, inserting a dissecting tool through the trocars and dissecting an area of the penis, abdominal or pelvic or retroperitoneal surroundings, and placing an adjustable restriction device in the dissected area, so that the restriction device engages the corpora cavernosa or crura or the prolongations thereof.

The method may further comprise hydraulically adjusting the restriction device in a non-manual manner. The restriction device may engage (a) both of the corpora cavernosa or crura or the prolongations thereof as a single unit; or (b) one of the exit veins from the penis.

Alternatively, the method may further comprise implanting (a) a further adjustable restriction device, wherein the two restriction devices engage the two corpora cavernosa or crura of the penis or their prolongations, respectively, as separate units; or (b) several restriction devices engaging respective exit veins from the penis.

The method may further comprise implanting a source of energy in the patient and providing a control device for controlling the source of energy from outside the patient's body to supply energy to the restriction device, and optionally also to other energy consuming components of the apparatus, with wirelessly transmitted energy from outside the patient's body.

The operation device may preferably be powered with electricity and operated in a non-manual manner.

The invention is described in more detail in the following with reference to the accompanying drawings, in which FIGS. 1A-D are block diagrams of four different principal embodiments of the male sexual impotence treatment apparatus according to the invention.

FIG. 2A-D are cross-sectional views of a pump mechanism according to FIG. 1C, which is designed to pump fluid in opposite directions by mechanically pushing a wall portion in only one direction.

FIG. 3 is a cross-sectional view of a reservoir having a variable volume controlled by a remote control motor, in accordance with a particular embodiment of the principal embodiment shown in FIG. 1B or 2B.

FIG. 4 is a cross-sectional view of a reservoir having a variable volume adjustable by manual manipulation, in accordance with a particular embodiment of the principal embodiment shown in FIG. 1B or 1D.

FIG. 5A is a perspective view of a hydraulic, pneumatic or mechanical servo system in accordance with a particular embodiment of the principal embodiment shown in FIG. 1D.

FIG. 5B is a cross-sectional view taken along line VB-VB of FIG. 5A.

Referring to the drawing figures, like reference numerals designate identical or corresponding elements throughout the several figures.

Figure 1A:
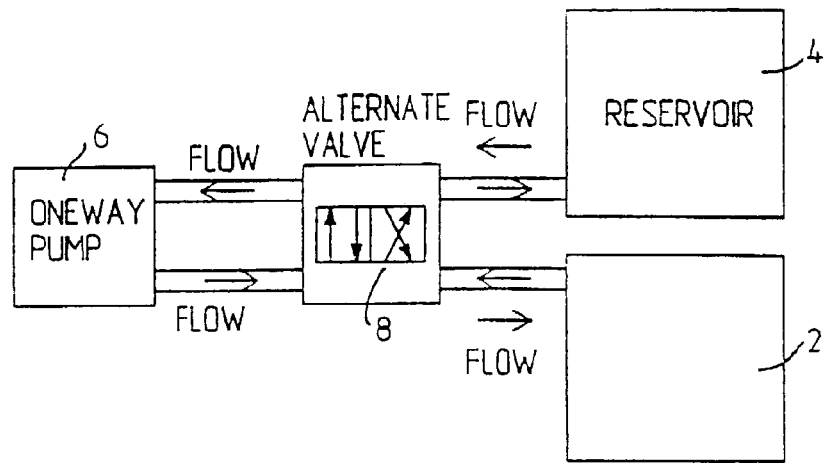
Figure 1B:
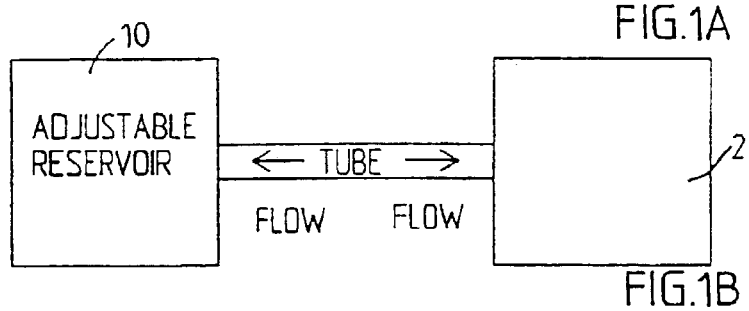
Figure 1C:
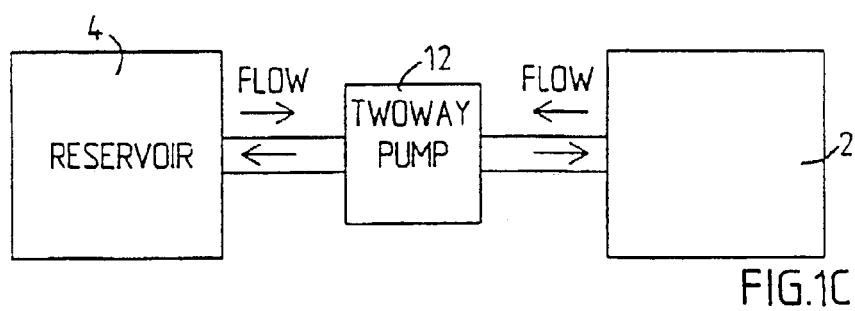
Figure 1D:
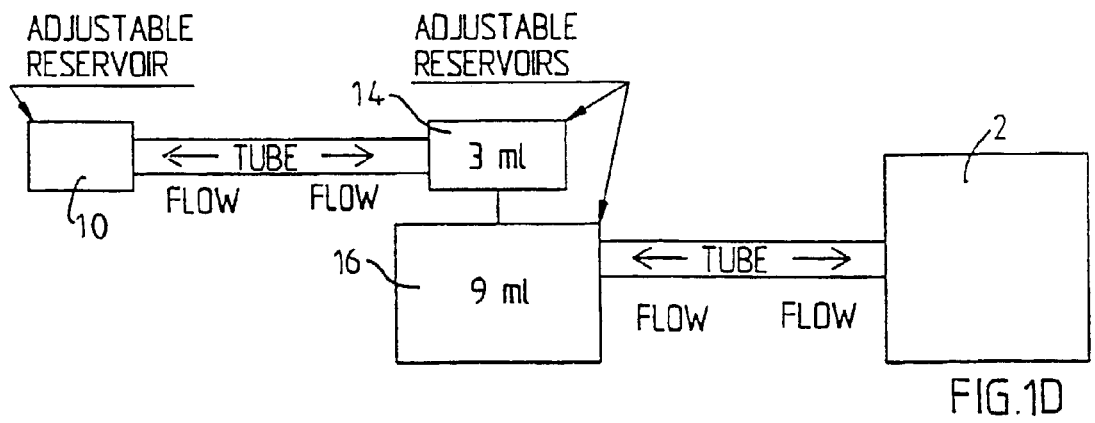
Figure 8:
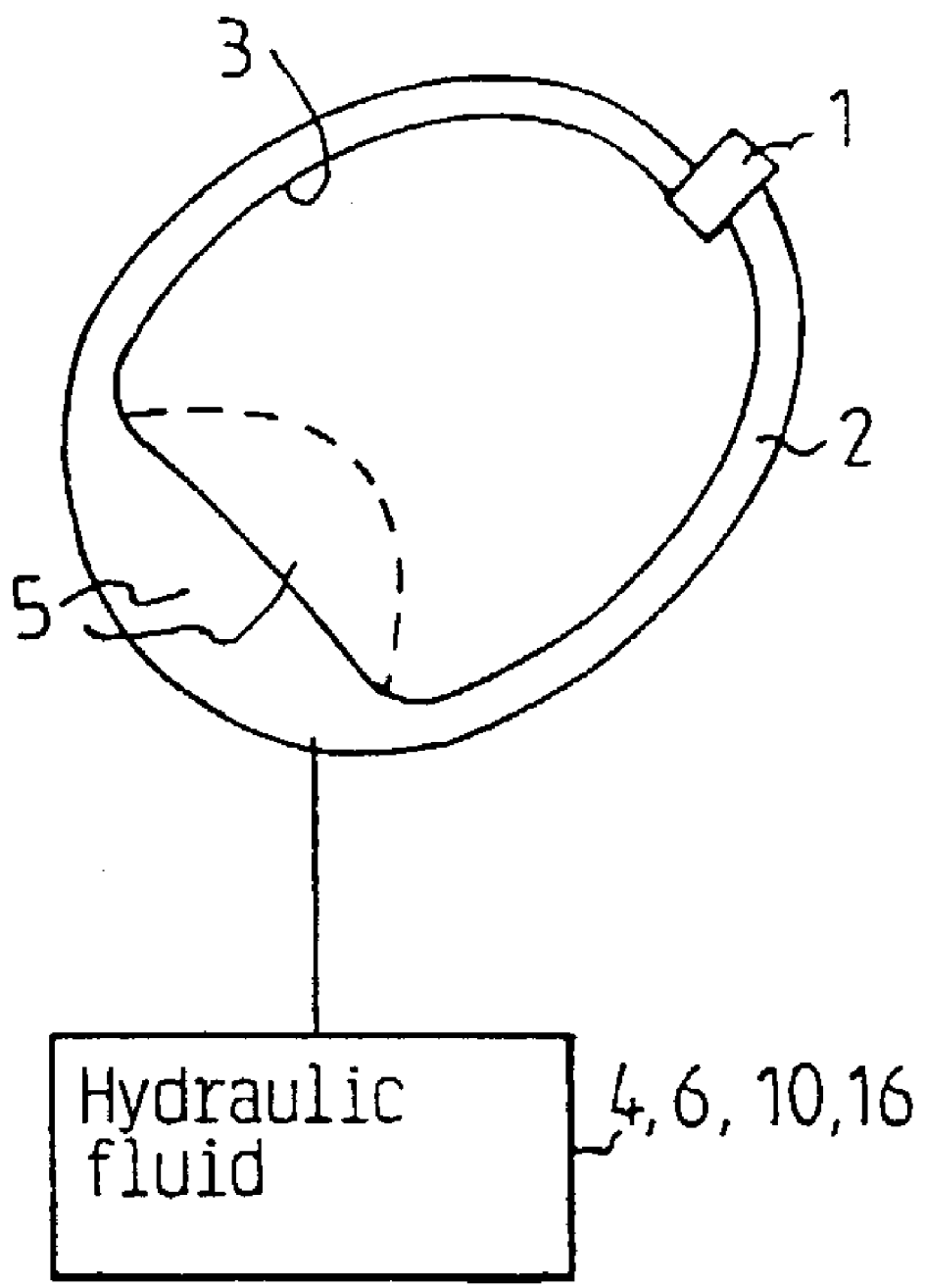
FIG. 8 is a schematic view af a band with a cavity defining a restriction opening for use in accordance with the invention.

FIGS. 1A-D are a block diagrams of four different embodiments of the male sexual impotence treatment apparatus according to the invention. FIG. 1A shows an elongated restriction member in the form of a band 2 forming a loop which defines a restriction opening. The band 2 provides a restricted blood through-flow area in the corpora cavernosa when applied around the latter. FIG. 1A further shows a separate reservoir 4, a one way pump 6 and an alternate valve 8. FIG. 1B shows the band 2 and a fluid supply reservoir 10. FIG. 1C shows the band 2, a two-way pump 12 and the reservoir 4. FIG. 1D shows a servo system with a first closed system controlling a second system. The servo system comprises the fluid supply reservoir 10 and a servo reservoir 14. The servo reservoir 14 controls a larger adjustable reservoir 16 which in connection with the band 2 applied around the corpora cavernosa varies the volume of a cavity in the band, which in turn varies the restricted blood through-flow area in the corpora cavernosa. Such a band 2 forming the restriction opening 3 is illustrated schematically in FIG. 8. The band 2 comprises an adjustment device having an expandable/contractabe cavity 5 which is expanded or contracted by supplying hydraulic fluid (e.g. from reservoir 4, 6, 10, or 16), and the band 2 may be sutured in place, illustrated schematically at 7 in FIG. 8.

Figure 2A:
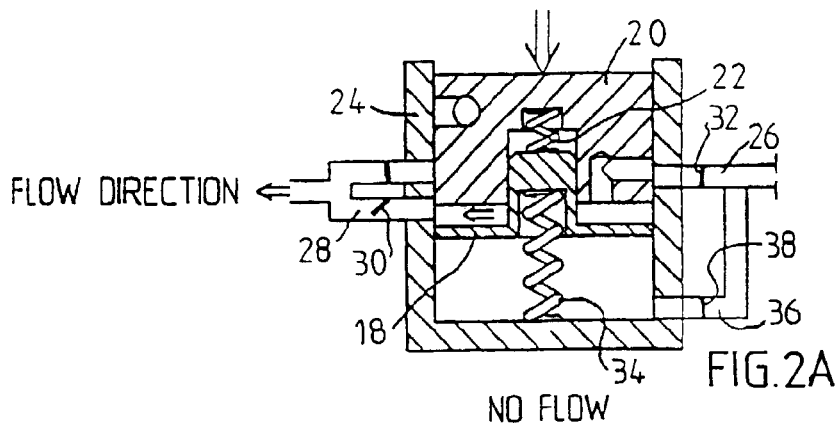
Figure 2B:
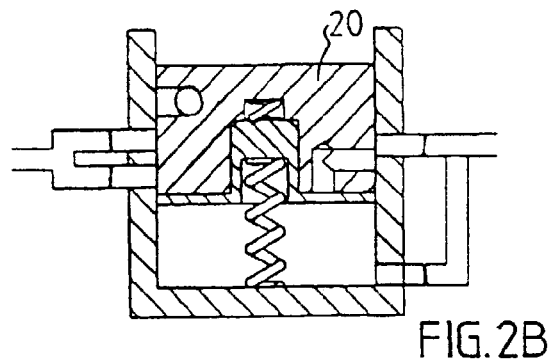
Figure 2C:
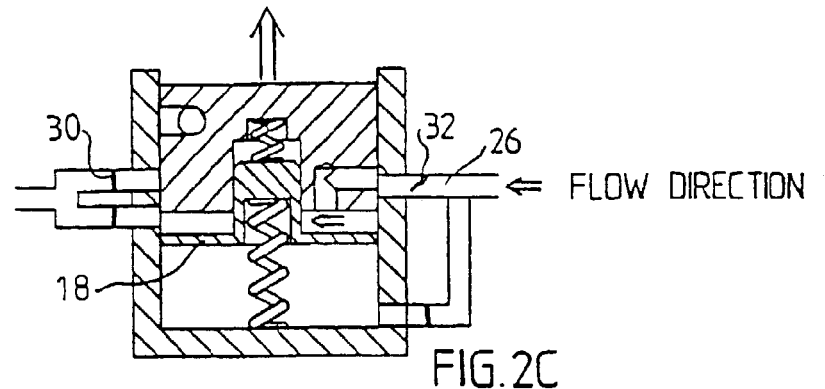
Figure 2D:
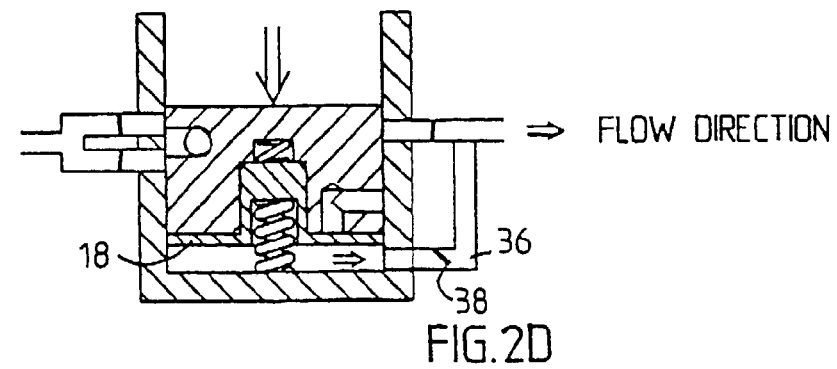

FIGS. 2A-D are cross-sectional views of a pump mechanism adapted to pump fluid in both directions only by mechanically pushing a separate sealing wall portion 18 in one direction. FIG. 2A shows a piston 20 pushed forwards against a spring 22 towards the wall portion 18 and located in a pump housing 24 conducting fluid from a right upper fluid passage 26 of the housing 24 to a left fluid passage 28 of the housing 24. A main valve 30 is open and a non-return valve 32 is closed. FIG. 2B illustrates the first pump movement in which the piston 20 has moved forwards and reaches the wall portion 18. FIG. 2C illustrates how the piston 20 moves backwards by the action of the spring 22. The main valve 30 is now closed and the non-return valve 32 is open for fluid from the right upper passage 26. FIG. 1D illustrates how the piston 20 is moved further downwards from its position according to FIG. 2B while pushing the wall portion 18 downwardly against a second spring 34 that is stronger than spring 22, whereby fluid escapes from a right lower fluid passage 36. When moving the piston 20 backwardly from the position according to FIG. 2D, fluid enters the left fluid passage 28 and a valve 38 in the lower right fluid passage 36 closes.

FIG. 3 is a cross-sectional view of a reservoir 40 defining a chamber 42, the volume of which is variable and is controlled by a remote controlled electric motor 44, in accordance with FIG. 1B or 1D. The reservoir 40 and the motor 44 are placed in a housing 46. The chamber 42 is varied by moving a large wall 48. The wall 48 is secured to a nut 50, which is threaded on a spindle 52. The spindle 52 is rotated by the motor 44 via an angular gearing, which comprises two conical gear wheels 54 and 56 in mesh with each other. The motor 44 is powered by a battery 58 placed in the housing 46. An signal receiver 60 for controlling the motor 44 is also placed in the housing 46. Alternatively, the battery 58 and the signal receiver 60 may be mounted in a separate place. The motor 44 may also be powered by energy transferred from transmitted signals.

FIG. 4 is a cross-sectional view of a reservoir 62 defining a chamber 64, the volume of which is variable and is controlled by manual manipulation. A gable wall portion 66 of an open ended inner cylindrical housing 68 is adapted to be pushed downwards to fit in a desired locking groove 70 of a plurality of locking grooves 70 on the mantle wall of the cylindrical housing 68, to reduce the volume of the chamber 64. The inner cylindrical housing 68 is suspended by springs 72 and is telescopically applied on an outer cylindrical housing 74. When pushing the inner cylindrical housing 68 it moves downwards relative to the outer cylindrical housing 74 causing the gable wall portion 66 to release from the locking groove 70 and move upwards relative to the inner cylindrical housing 68. When the inner housing 68 is moved upwardly by the action of the springs 72 the volume of the chamber 64 is increased.

FIGS. 5A and 5B show a servo means comprising a main ring-shaped fluid reservoir 76 defining a chamber 78, the volume of which is variable. Centrally positioned in the main ring-shaped reservoir 76 there is a servo fluid reservoir 80 defining a chamber 82, the volume of which is variable. The chamber 82 of the servo reservoir 80 is substantially smaller than the chamber 78 of the main reservoir 76. The two reservoirs 76 and 80 are situated between two opposite separate walls 84 and 86, and are secured thereto. When changing the amount of fluid in the servo reservoir 80, the two opposite walls 84,86 are moved towards or away from each other, whereby the volume of the chamber 78 of the main reservoir 76 is changed.

Figure 6:
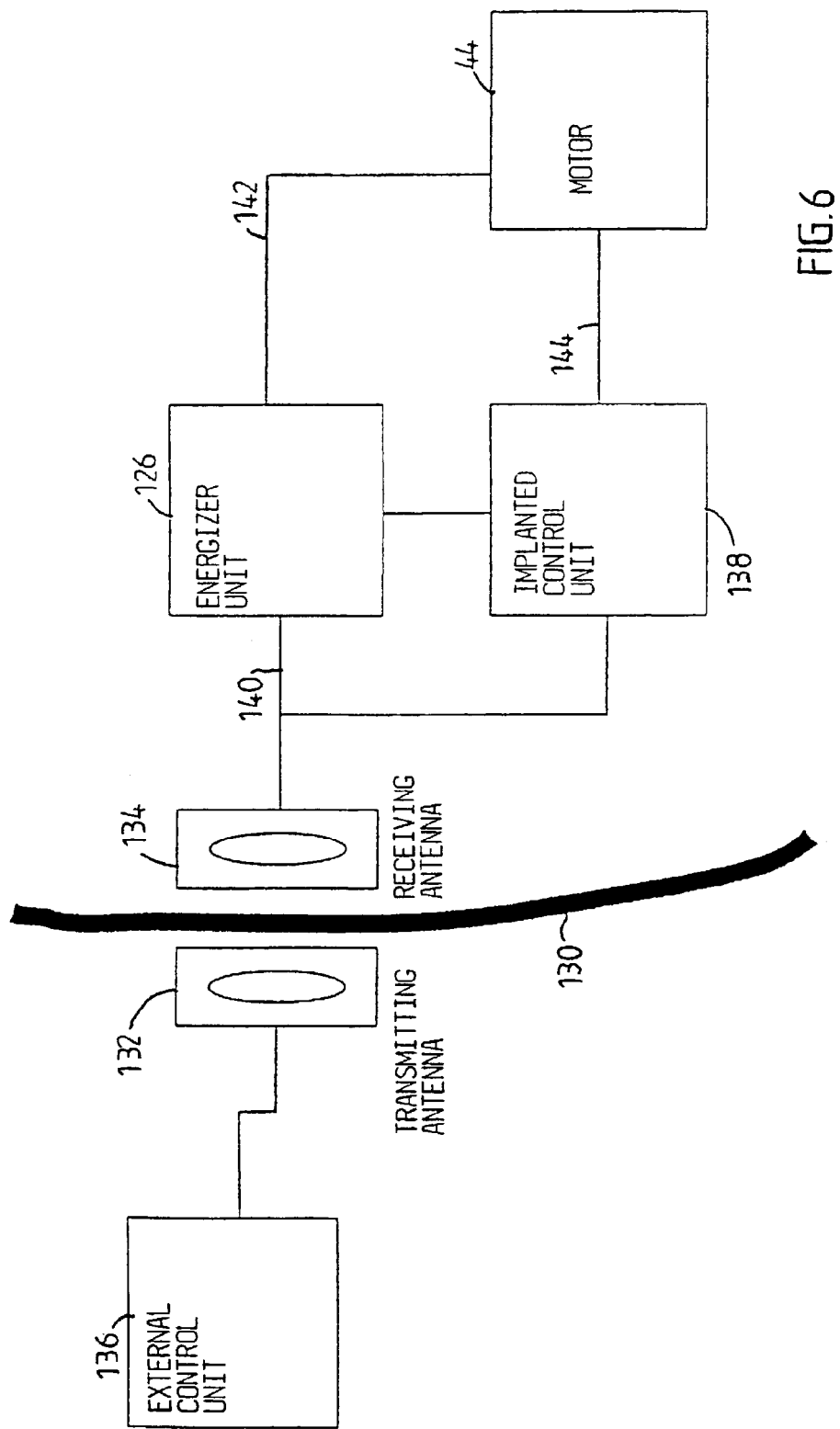
FIG. 6 is a block diagram illustrating remote control components of the device of the invention.

FIG. 6 shows the basic parts of a remote control system of the apparatus of the invention including the electric motor 44 of the embodiment shown in FIG. 3. In this case, the remote control system is based on the transmission of electromagnetic wave signals, often of high frequencies in the order of 100 kHz-1 gHz, through the skin 130 of the patient. In FIG. 6, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either increase or decrease the size of the restriction opening defined by the loop of the restriction member 2. The microprocessor starts a command by applying a high frequency signal on the antenna 132. After a short time, when the signal has energized the implanted parts of the control system, commands are sent to increase or decrease the size of the restriction opening of the restriction member 2 in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g. about 30 seconds or more). When a new increase or decrease step is desired the Count byte is increased by one to allow the implanted control unit 138 to decode and understand that another step is demanded by the external control unit 136. If any part of the digital packet is erroneous, its content is simply ignored.

Through a line 140, an implanted energiser unit 126 draws energy from the high frequency electromagnetic wave signal received by the receiving antenna 134. The energiser unit 126 stores the energy in a power supply, such as a large capacitor, powers the control unit 138 and powers the electric motor 44 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energiser unit 126 has sufficient energy stored, sends a signal via a signal line 144 to the motor 44 to either increase or decrease the size of the restriction opening of the restriction member 2 depending on the received command code.

Alternatively, the energy stored in the power supply of the energiser unit may only be used for powering a switch, and the energy for powering the motor 44 may be obtained from another implanted power source of relatively high capacity, for example a battery. In this case the switch is adapted to connect the battery to the control unit 138 in an on mode when the switch is powered by the power supply and to keep the battery disconnected from the control unit in a standby mode when said switch is unpowered.

Figure 7:
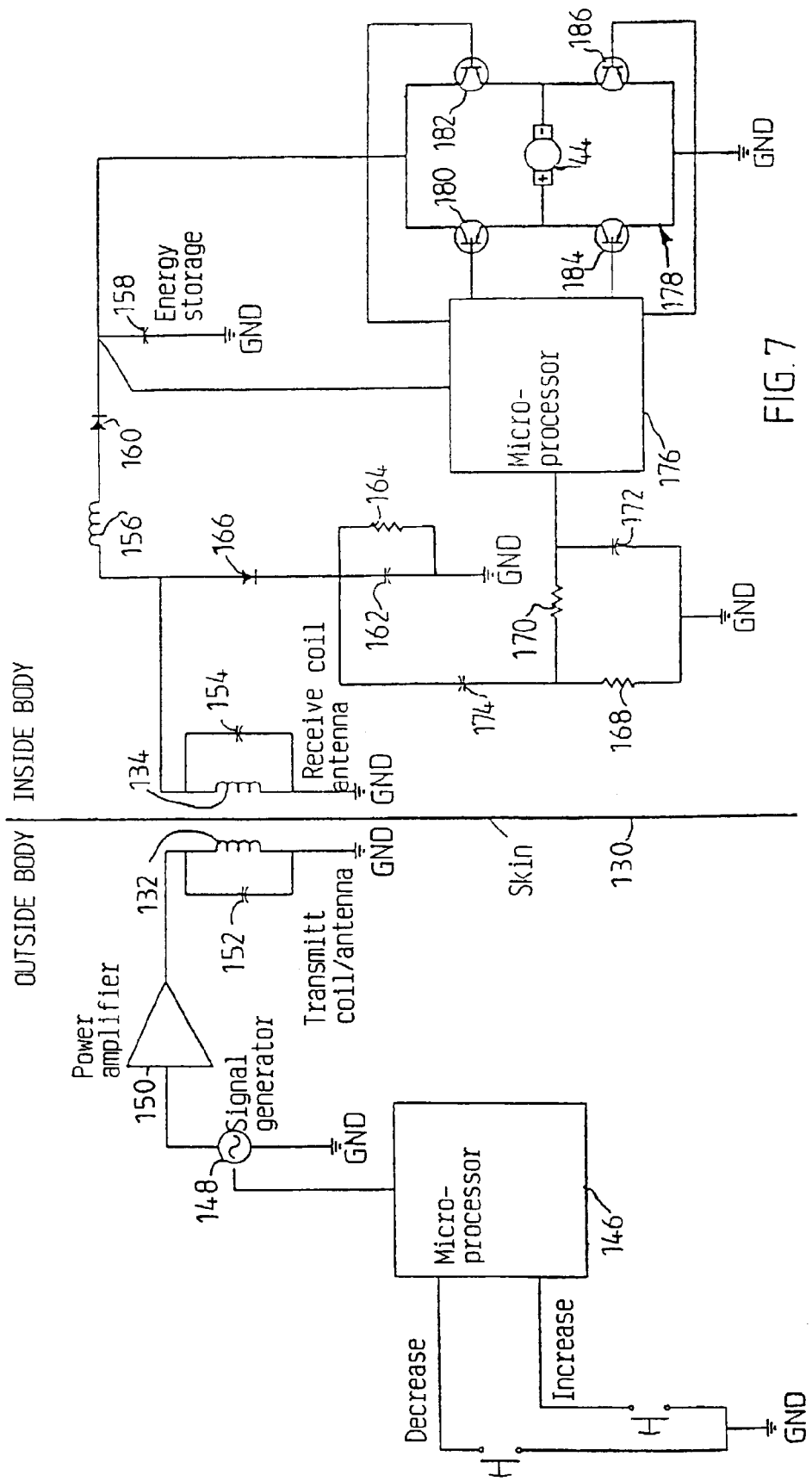
FIG. 7 is a schematic view of exemplary circuitry used for the block diagram in FIG. 4.

With reference to FIG. 7, the remote control system schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the restriction device. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168,170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 44 via an H-bridge 178 comprising transistors 180,182,184 and 186. The motor 44 can be driven in two opposite directions by the H-bridge 178.

The microprocessor 176 also monitors the amount of stored energy in the storage capacitor 158. Before sending signals to activate the motor 44, the microprocessor 176 checks whether the energy stored in the storage capacitor 158 is enough. If the stored energy is not enough to perform the requested operation, the microprocessor 176 waits for the received signals to charge the storage capacitor 158 before activating the motor 44.

Figure 9A:
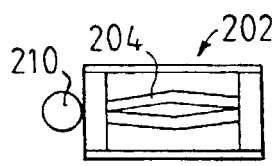
FIGS. 9A and 9B are schematic views of a first mechanical restriction device for use in accordance with the invention.
Figure 9B:
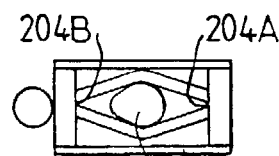

FIGS. 9A and 9B show an embodiment of the apparatus of the invention comprising a restriction device 202 having an elongated flexible restriction member 204, such as a belt, a cord or the like. The flexible member 204 extends in a loop around the corpora cavernosa. (Alternatively, the flexible member 204 may comprise two separate parts on opposite sides of the corpora cavernosa.) One portion 204A of member 204 is attached to a frame 208 and another portion 204B of member 204 opposite portion 204A in the loop of the flexible member 204 is connected to an adjustment device 210, which is fixed to the frame 208. The adjustment device 210 pulls the flexible member 204 away from portion 204A to squeeze the corpora cavernosa between two opposite lengths of the flexible member 204 to thereby restrict the blood flow leaving the penis, see FIG. 9A, and releases the corpora cavernosa from the flexible member 204 to thereby increase the blood flow leaving the penis, see FIG. 9B.

Figure 10A:
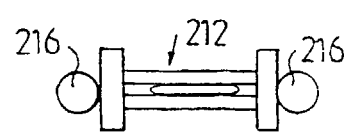
FIGS. 10A and 10B are schematic views of a second mechanical restriction device for use in accordance with the invention.
Figure 10B:
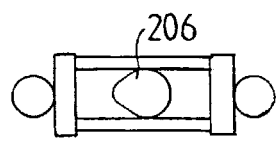

FIGS. 10A and 10B show an embodiment of the apparatus of the invention comprising a restriction device 212 having two plate or bar elements 214 on opposite sides of the corpora cavernosa 206. An adjustment device 216 moves the elements 212 in parallel towards each other to squeeze the corpora cavernosa 206 between the elements 212 to thereby restrict the blood flow leaving the penis, see FIG. 10A, and moves the elements 212 away from each other to increase the blood flow leaving the penis, see FIG. 10B.

Figure 11:
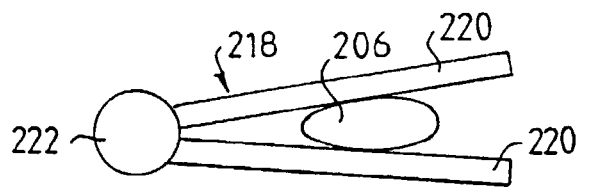
FIG. 11 is a schematic view of a third mechanical restriction device for use in accordance with the invention.

FIG. 11 shows an embodiment of the apparatus of the invention comprising a restriction device 218 having two articulated clamping elements 220 positioned on opposite sides of the corpora cavernosa 206. An adjustment device 222 moves the clamping elements 220 toward each other to clamp the corpora cavernosa 206 between the clamping elements 220 to thereby restrict the blood flow leaving the penis, and moves the clamping elements 220 away from each other to release the corpora cavernosa 206 from the clamping elements 220 to thereby increase the blood flow leaving the penis.

Figure 12A:
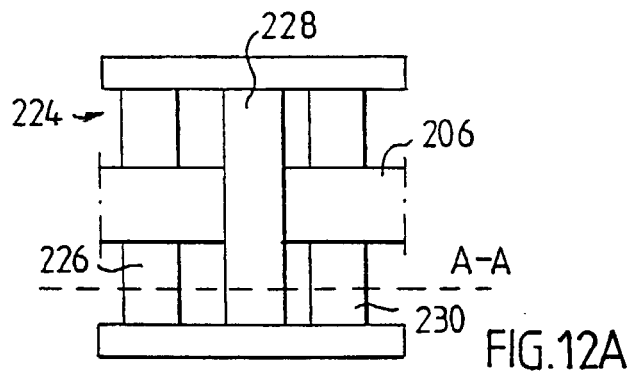
FIG. 12A is a schematic front view of a fourth mechanical restriction device for use in accordance with the invention.
Figure 12B:
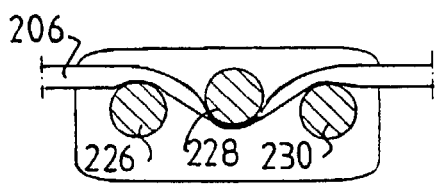
FIGS. 12B and 12C are sectional views along the line A-A of FIG. 12A.
Figure 12C:
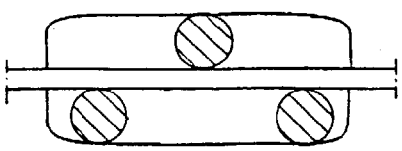

FIGS. 12A, 12B and 12C show an embodiment of the apparatus of the invention comprising a restriction device 224 having three bending members in the form of cylindrical rollers 226, 228 and 230 displaced relative one another in a row along the corpora cavernosa 206 and positioned alternately on opposite sides of the corpora cavernosa 206. (Alternatively, each roller 226, 228 and 230 may take the shape of an hour-glass.) An adjustment device 232 moves the two outer rollers 226,230 laterally against the corpora cavernosa 206 in one direction and the intermediate roller 228 against the corpora cavernosa 206 in the opposite direction to bend the corpora cavernosa to thereby restrict the blood flow leaving the penis, see FIG. 12B. To release the corpora cavernosa from the rollers 226-230, the adjustment device 232 moves the rollers 226-230 away from the corpora cavernosa 206, see FIG. 12C.

Figure 13A:
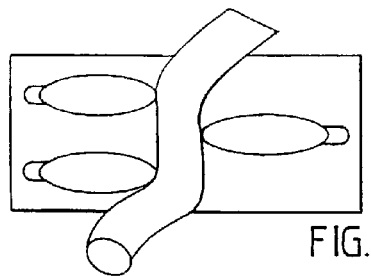
FIGS. 13A through 17B are five modifications of the embodiment of FIGS. 12A-12C.
Figure 13B:
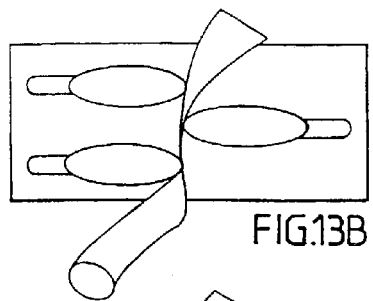
Figure 14A:
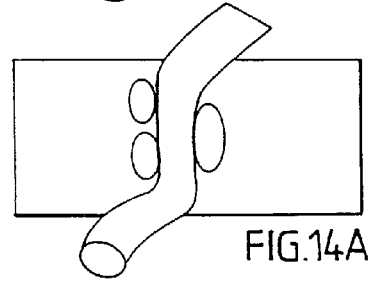
Figure 14B:
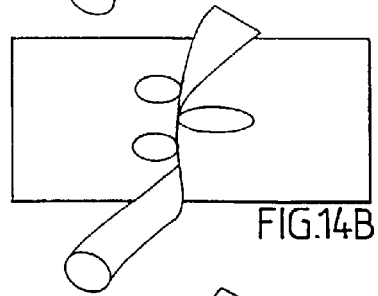
Figure 15A:
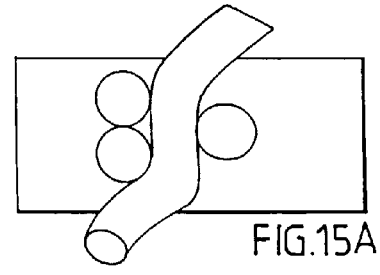
Figure 15B:
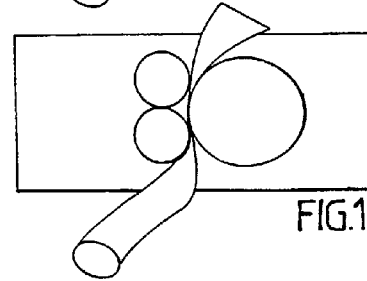
Figure 16A:
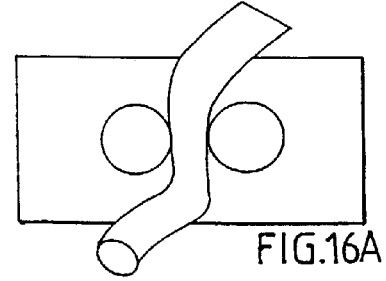
Figure 16B:
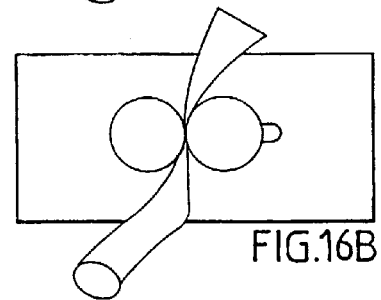
Figure 17A:
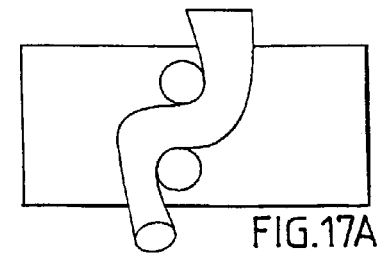
Figure 17B:
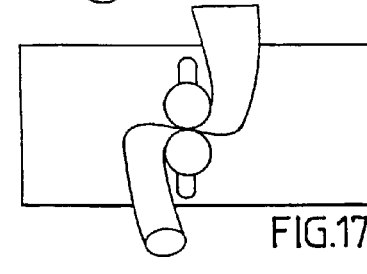

FIGS. 13A through 17B schematically illustrates modifications of the above embodiment according to FIGS. 12A-12C. Thus, FIGS. 13A and 13B show an embodiment similar to that of FIGS. 12A-12C except that the bending members are oval and not rotatable. FIGS. 14A and 14B show an embodiment similar to that of FIGS. 13A and 13B except that the oval bending members are rotatable to squeeze the corpora cavernosa, see FIG. 14B, and to release the corpora cavernosa, see FIG. 14A. FIGS. 15A and 15B show an embodiment similar to that of FIGS. 12A-12C except that the intermediate roller has a changeable diameter to squeeze the corpora cavernosa, see FIG. 15B, and to release the corpora cavernosa, see FIG. 15A. FIGS. 16A and 16B show an embodiment similar to that of FIGS. 10A-10C except that the elements are replaced by two cylindrical rollers positioned on opposite sides of the corpora cavernosa. Finally, FIGS. 17A and 17B show an embodiment substantially similar to that of FIGS. 16A and 16B except that the restriction device is turned 90 to form an S-shaped curvature of the corpora cavernosa.

Figure 18:
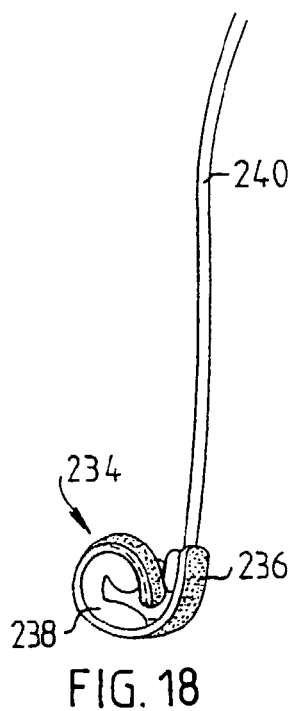
FIG. 18 is a view of an inflatable restriction device of the apparatus of the invention.

FIG. 18 shows an example of a hydraulic restriction device 234 for use in accordance with the invention. The restriction device 234 comprises an elongated restriction member 236 having an inflatable cavity 238. A tube 240 connects the cavity 238 to a hydraulic fluid reservoir, not shown. The restriction member 236 may be wrapped around the corpora cavernosa. Alternatively, two restriction members 236 may be wrapped around the respective crura.

Figure 19:
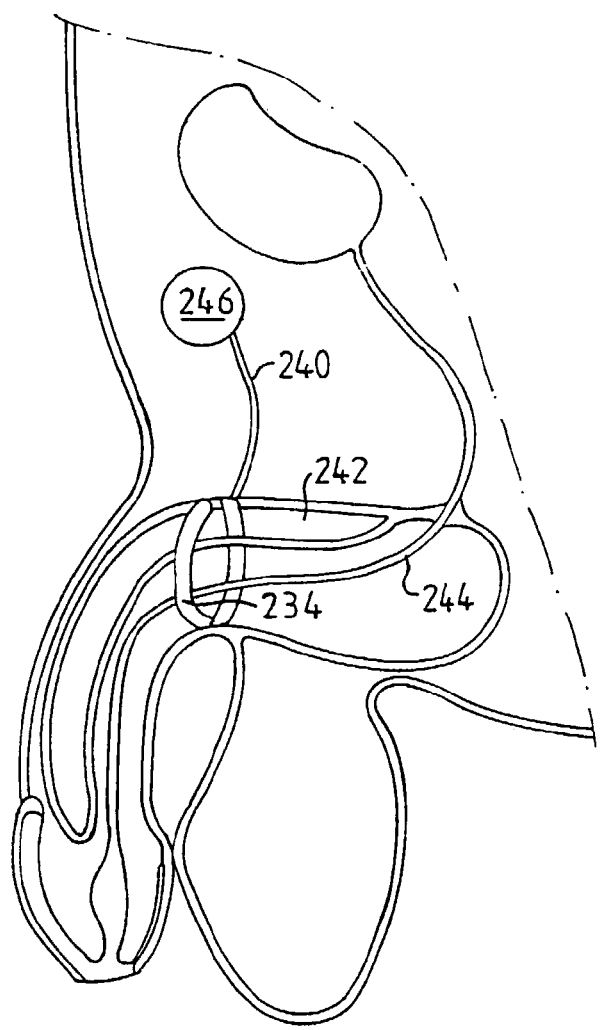
FIG. 19 illustrates the apparatus of the invention implanted in a patient.

FIG. 19 schematically illustrates how any of the above-described embodiments of the male sexual impotence treatment apparatus of the invention can be implanted in a patient. Thus, an implanted adjustable hydraulic restriction device 234 extends almost completely around the corpora cavernosa 242 and the urethra 244 to be capable of contracting the corpora cavernosa 242 as a single unit. An adjustment device in the form of an inflatable cavity in the restriction device 234 is adapted to adjust the restriction device 234 so that the blood flow leaving the penis is restricted. An implanted assembly 246 includes a hydraulic fluid reservoir and a hydraulic operation device (which may include a pump) for distributing hydraulic fluid between the reservoir and the inflatable/contractible cavity of the restriction device 234 via a fluid conduit 240.

A wireless remote control of the apparatus comprises an external signal transmitter 248, which may comprise a hand-held unit, and an implanted signal receiver, which is incorporated in the implanted assembly 246. The assembly 246 further includes a control unit for controlling the restriction device 234 in response to a control signal from the external transmitter. The signal receiver of the assembly 246 further includes an energiser unit which transforms energy from the control signal transmitted by the external transmitter into electric energy for powering the operation device of the assembly 246 and for energy consuming implanted components of the apparatus.

A pressure sensor 250 is implanted for sensing the pressure on the restriction device 234. The control unit of the assembly 246 controls the operation device of the assembly 246 to operate the adjustment device 234 to adjust the restriction device 234 so that the corpora cavernosa is released in response to the pressure sensor 250 sensing an abnormal high pressure.

There is a number of conceivable alternative embodiments of the invention that give the same result as the above-described embodiments. For example, the microprocessor of the external and implanted, respectively, control units may be replaced by discrete components. The power amplifier of the external control unit may be omitted if the signals generated by the signal generator are strong enough. Therefore, the invention is to be accorded the broadest interpretation of the appended claims to encompass all equivalent structures and assemblies.

The invention claimed is:

1. A male sexual impotence treatment apparatus, comprising
   an adjustable restriction device implantable in a male patient, who suffers from sexual impotence, for engaging the corpora cavernosa or crura or the prolongations thereof of the patient's penile tissue;
   an implantable adjustment device for adjusting the restriction device to temporarily contract the corpora cavernosa or crura or the prolongations thereof to restrict the blood flow leaving the penis;
   an implantable powered, non-manual operation device for operating the adjustment device; and
   an implantable reservoir containing hydraulic fluid, wherein the operation device operates the adjustment device by distributing the hydraulic fluid to and from the reservoir.

2. A male sexual impotence treatment apparatus according to claim 1, wherein the restriction device is adapted to restrict the corpora cavernosa or crura or the prolongations thereof as a single unit.

3. An apparatus according to claim 1, wherein the reservoir contains a predetermined amount of hydraulic fluid.

4. An apparatus according to claim 1, wherein the adjustment device comprises an expandable cavity in the restriction device, the corpora cavernosa or crura or the prolongation thereof being contracted upon expansion of the cavity and released upon contraction of the cavity, and the hydraulic operation device is adapted to distribute hydraulic fluid from the reservoir to expand the cavity, and to distribute hydraulic fluid from the cavity to the reservoir to contract the cavity.

5. An apparatus according to claim 4, wherein the reservoir defines a chamber for said predetermined amount of fluid and the operation device is adapted to change the size of the chamber.

6. An apparatus according to claim 5 wherein the operation device comprises first and second wall portions of the reservoir and is adapted to provide relative displacement between the first and second wall portions of the reservoir, in order to change the volume of the chamber.

7. An apparatus according to claim 6, wherein the operation device is adapted to provide said relative displacement in response to the pressure in the reservoir.

8. An apparatus according to claim 7, wherein the operation device comprises a pressure controlled hydraulic operation device.

9. An apparatus according to claim 8, further comprising an alarm adapted to generate an alarm signal in response to the lapse of a predetermined time period during which the pressure controlling the hydraulic operation device exceeds a predetermined high value.

10. An apparatus according to claim 6, wherein the first and second wall portions of the reservoir are displaceable relative to each other by magnetic means, hydraulic means, or electric control means, or a combination thereof.

11. An apparatus according to claim 6, wherein the operation device is adapted to distribute fluid from the reservoir to the cavity of the restriction device in response to a predetermined first displacement of the first wall portion of the reservoir relative to the second wall portion of the reservoir and to distribute fluid from the cavity to the reservoir in response to a predetermined second displacement of the first wall portion relative to the second wall portion.

12. An apparatus according to claim 4, wherein the operation device comprises a pump adapted to pump fluid between the reservoir to the cavity of the restriction device.

13. An apparatus according to claim 12, wherein the pump comprises a first activation member for activating the pump to pump fluid from the reservoir to the cavity of the restriction device and a second activation member for activating the pump to pump fluid from the cavity to the reservoir.

14. An apparatus according to claim 13, wherein at least one of the activation members is adapted to operate when subjected to a predetermined external pressure.

15. An apparatus according to claim 13, wherein at least one of the first and second activating members are operable by magnetic means, hydraulic means, electric control means or manual manipulation means, or a combination thereof.

16. An apparatus according to claim 1, wherein the operation device comprises a servo means.

17. An apparatus according to claim 6 wherein the operation device comprises a reverse servo.

18. A male sexual impotence treatment apparatus, comprising an adjustable restriction device implantable in a male patient, who suffers from sexual impotence, for engaging the corpora cavernosa or crura or the prolongations thereof of the patient's penile tissue, an implantable adjustment device for adjusting the restriction device to temporarily contract the corpora cavernosa or crura or the prolongations thereof to restrict the blood flow leaving the penis, and an implantable operation device for operating the adjustment device, characterised in that the operation device comprises a servo means.

19. An apparatus according to claim 18, wherein the operation device is powered.

20. An apparatus according to claim 18, wherein the operation device is manually operated.

21. An apparatus according to claim 16, wherein the servo means comprises a motor, preferably an electric motor.

22. An apparatus according to claim 21, wherein the motor is reversible.

23. An apparatus according to claim 21, further comprising a gearing connected between the motor and the adjustment device.

24. An apparatus according to claim 18, further comprising an implantable reservoir defining a chamber for hydraulic fluid, wherein the operation device is adapted to operate the adjustment device by using the hydraulic fluid of the reservoir.

25. An apparatus according to claim 1, wherein the reservoir contains a predetermined amount of hydraulic fluid.

26. An apparatus according to claim 18 wherein the servo means comprises a reverse servo.

27. An apparatus according to claim 17, wherein the reservoir comprises first and second wall portions and the reverse servo is adapted to provide relative displacement between the first and second wall portions of the reservoir, in order to change the volume of the reservoir.

28. An apparatus according to claim 27 and, wherein the reverse servo device is adapted to provide said relative displacement in response to the pressure in the reservoir.

29. An apparatus according to claim 18, wherein the servo means comprises a pressure controlled servo means.

30. An apparatus according to claim 29, further comprising an alarm adapted to generate an alarm signal in response to the lapse of a predetermined time period during which the pressure controlling the servo means exceeds a predetermined high value.

31. An apparatus according to claim 26, wherein the reverse servo comprises magnetic means, electric means or manual manipulation means or a combination thereof.

32. An apparatus according to claim 27, wherein the reverse servo comprises hydraulic means.

33. An apparatus according to claim 32, wherein the reverse servo further comprises a servo reservoir defining a chamber containing servo fluid, and the operation device comprise first and second wall portions of the servo reservoir, which are displaceable relative to each other to change the volume of the chamber of the servo reservoir.

34. An apparatus according to claim 33, wherein the first and second wall portions of the servo reservoir are displaceable relative to each other by magnetic means, hydraulic means, or electric control means.

35. An apparatus according to claim 32, wherein the reverse servo comprises a servo reservoir and a fluid supply reservoir connected in a closed system and containing a further predetermined amount of fluid.

36. An apparatus according to claim 35, wherein the fluid supply reservoir defines a chamber for the further predetermined amount of fluid and the hydraulic operation device is adapted to change the volume of the chamber and thereby control the amount of fluid in the servo reservoir.

37. An apparatus according to claim 36, wherein the fluid supply reservoir comprises first and second wall portions, which are displaceable relative to each other to change the volume of the chamber of the fluid supply reservoir.

38. An apparatus according to claim 37, wherein the fluid supply reservoir increases the amount of fluid in the servo reservoir in response to a predetermined first displacement of the first wall portion of the fluid supply reservoir relative to the second wall portion of the fluid supply reservoir and decreases the amount of fluid in the servo reservoir in response to a predetermined second displacement of the first wall portion of the fluid supply reservoir relative to the second wall portion of the fluid supply reservoir.

39. A male sexual impotence treatment apparatus comprising:
an adjustable restriction device implantable in a male patient, who suffers from sexual impotence, for engaging the corpora cavernosa or crura or the prolongations thereof of the patient's penile tissue;
an implantable adjustment device for adjusting the restriction device to temporarily contract the corpora cavernosa or crura or the prolongations thereof to restrict the blood flow leaving the penis;
an implantable powered, non-manual operation device for operating the adjustment device; and
wherein the adjustment device comprises a hydraulic adjustment device, and further comprising a reservoir implantable in the patient and containing a predetermined amount of hydraulic fluid, and a conduit providing fluid connection between the reservoir and the hydraulic adjustment device, the operation device being adapted to operate the hydraulic adjustment device by distributing hydraulic fluid through the conduit between the reservoir and the hydraulic adjustment device, the conduit and hydraulic adjustment device being devoid of any non-return valve to permit free flow of hydraulic fluid in both directions in the conduit.

40. An apparatus according to claim 39, wherein the reservoir forms a fluid chamber with a variable volume, and the operation device is adapted to distribute fluid from the chamber to the adjustment device by reduction of the volume of the chamber and to withdraw fluid from the adjustment device by expansion of the volume of the chamber.

41. An apparatus according to claim 40, wherein the operation device comprises a motor or a pump.

42. An apparatus according to claim 40, wherein the operation device comprises a movable wall of the reservoir for changing the volume of the chamber.

43. An apparatus according to claim 42, wherein the operation device is adapted to change the volume of the chamber by moving the movable wall in response to the pressure in the chamber.

44. An apparatus according to claim 5, further comprising an injection port subcutaneously implantable in the patient and in fluid communication with the chamber.

45. An apparatus according to claim 44, wherein the injection port is integrated in the reservoir.

46. A male sexual impotence treatment apparatus comprising:
an adjustable restriction device implantable in a male patient, who suffers from sexual impotence, for engaging the corpora cavernosa or crura or the prolongations thereof of the patient's penile tissue;
an implantable adjustment device for adjusting the restriction device to temporarily contract the corpora cavernosa or crura or the prolongations thereof to restrict the blood flow leaving the penis;
an implantable powered, non-manual operation device for operating the adjustment device; and
wherein the restriction device comprises an elongated restriction member and forming means for forming the restriction member into at least a substantially closed loop around the corpora cavernosa or crura or the prolongations thereof, the loop defining a restriction opening, whereby the adjustment device is adapted to adjust the restriction member in the loop to change the size of the restriction opening.

47. An apparatus according to claim 46, wherein the forming means forms the restriction member into a loop having a predetermined size or a size selected from several predetermined sizes.

48. An apparatus according to claim 46, wherein the adjustment device is adapted to change the size of the restriction opening such that the outer circumferential confinement surface of the restriction member is changed.

49. An apparatus according to claim 46, wherein the adjustment device is adapted to change the size of the restriction opening such that the outer circumferential confinement surface of the restriction member is unchanged.

50. An apparatus according to claim 46, wherein the restriction member is non-inflatable, and the adjustment device is adapted to adjust the restriction member in said loop.

51. An apparatus according to claim 34, wherein the adjustment device mechanically adjusts the restriction member.

52. An apparatus according to claim 50, wherein the adjustment device hydraulically adjusts the non-inflatable restriction member.

53. An apparatus according to claim 51, wherein the elongated restriction member is flexible, and the adjustment device is adapted to pull a first portion of the flexible restriction member from a second portion of the flexible restriction member opposite the first portion in the loop to squeeze the corpora cavernosa or crura or the prolongations thereof between two opposite lengths of the elongated flexible restriction member to restrict the blood flow leaving the penis, and to release the corpora cavernosa or crura or the prolongations thereof from the flexible restriction member to restore the blood flow.

54. An apparatus according to claim 1, wherein the adjustment device mechanically adjusts the restriction device.

55. An apparatus according to claim 1, wherein the restriction device comprises at least two elements to be placed on different sides of the corpora cavernosa or crura or the prolongations thereof, and the adjustment device is adapted to squeeze the corpora cavernosa or crura or the prolongations thereof between the elements to restrict the blood flow leaving the penis, and to release the corpora cavernosa or crura or the prolongations thereof from the elements to restore the blood flow.

56. An apparatus according to claim 1, wherein the restriction device comprises at least two articulated clamping elements to be positioned on opposite or different sides of the corpora cavernosa or crura or the prolongations thereof, and the adjustment device is adapted to turn the clamping elements toward each other to clamp the corpora cavernosa or crura or the prolongations thereof between the clamping elements to restrict the blood flow leaving the penis, and to turn the clamping elements away from each other to release the corpora cavernosa or crura or the prolongations thereof from the elements to restore the blood flow.

57. An apparatus according to claim 1, wherein the restriction device is adapted to bend a portion of the corpora cavernosa or crura or the prolongations thereof.

58. An apparatus according to claim 41, wherein the restriction device comprises at least two bending members to be positioned on opposite sides of the corpora cavernosa or crura or the prolongations thereof and to be displaced relative to each other along the corpora cavernosa or crura or the prolongations thereof in the corpora cavernosa or crura or the prolongations thereof, and the adjustment device is adapted to move the bending members against the corpora cavernosa or crura or the prolongations thereof to bend them to restrict the blood flow leaving the penis, and to move the bending members away from the corpora cavernosa or crura or the prolongations thereof to release them from the bending members to restore the blood flow.

59. An apparatus according to claim 42, wherein the bending members comprise rollers.

60. An apparatus according to claim 1, wherein the restriction device is adapted to rotate a portion of the corpora cavernosa or crura or the prolongations thereof.

61. An apparatus according to claim 1, further comprising a wireless remote control for non-invasively controlling the hydraulic operation device.

62. An apparatus according to claim 61, wherein the remote control comprises an external wireless hand-held remote control unit which is manually operable by the patient to control the restriction device to squeeze or release the corpora cavernosa or crura or the prolongations thereof.

63. An apparatus according to claim 62, wherein the remote control comprises an external signal transmitter, receiver or transceiver and a signal receiver, transmitter or transceiver implantable in the patient.

64. An apparatus according to claim 63, wherein the signal receiver and/or transmitter comprises a control unit adapted to control the operation device in response to a control signal received from the signal transmitter.

65. An apparatus according to claim 64, further comprising an implantable energizer unit for providing energy to energy consuming implantable components of the apparatus.

66. A male sexual impotence treatment apparatus comprising:
an adjustable restriction device implantable in a male patient, who suffers from sexual impotence, for engaging the corpora cavernosa or crura or the prolongations thereof of the patient's penile tissue;
an implantable adjustment device for adjusting the restriction device to temporarily contract the corpora cavernosa or crura or the prolongations thereof to restrict the blood flow leaving the penis;
an implantable powered, non-manual operation device for operating the adjustment device; and
wherein the operation device comprises a motor for operating the adjustment device.

67. An apparatus according to claim 65, wherein the control unit is adapted to power the motor with energy provided by the energizer unit in response to a control signal received from the signal transmitter.

68. An apparatus according to claim 61, wherein the remote control comprises wireless energy transfer means for transferring energy from outside the patient's body to energy consuming implantable components of the apparatus.

69. An apparatus according to claim 65, wherein the energy transfer means comprises an implantable energizer unit, which is adapted to transform energy from the control signal, as it is transmitted to the signal receiver, into electric energy.

70. An apparatus according to claim 68, wherein the operation device comprises a motor, and the wireless energy transfer means is adapted to directly power the motor with transferred energy.

71. An apparatus according to claim 69, wherein the energy transferred by the wireless energy transfer means comprises a signal.

72. An apparatus according to claim 71, wherein the signal comprises a wave signal.

73. An apparatus according to claim 69, wherein the energy transferred by the wireless energy transfer means comprises an electric field or a magnetic field or a combination thereof.

74. An apparatus according to claim 71, wherein the signal is analog or digital or a combination thereof.

75. An apparatus according to claim 63, wherein the signal transmitter and signal receiver are adapted to transmit and receive an analog or digital signal or a combination thereof.

76. An apparatus according to claim 75, wherein the signal comprises analog or digital pulses.

77. An apparatus according to claim 74, wherein the analog or digital signal comprises a magnetic field or an electric field or a combination thereof.

78. An apparatus according to claim 63, wherein the signal transmitter and signal receiver are adapted to transmit and receive a wave signal.

79. An apparatus according to claim 71, wherein the wave signal comprises an electromagnetic wave signal, a sound wave signal or a carrier wave signal for a remote control signal or a combination thereof.

80. An apparatus according to claim 79, wherein the carrier signal is frequency, amplitude or frequency and amplitude modulated.

81. An apparatus according to claim 71 wherein the energy transfer means transfers the energy from the signal into a direct, pulsating direct or alternating current or a combination thereof.

82. An apparatus according to claim 61, wherein the remote control is capable of obtaining information related to important parameters of the apparatus from inside the patient's body and of commanding the adjustment device to adjust the restriction device in response to obtained information.

83. An apparatus according to claim 61, wherein the remote control is capable of obtaining information related to the contraction of the corpora cavernosa or crura or the prolongations thereof and of commanding the adjustment device to adjust the restriction device in response to obtained information.

84. An apparatus according to claim 1, further comprising an implantable source of energy for powering the operation device and/or for energizing other energy consuming components of the apparatus, wherein the energy from the source of energy is releasable from outside the patient's body.

85. A male sexual impotence treatment apparatus comprising:
an adjustable restriction device implantable in a male patient, who suffers from sexual impotence, for engaging the corpora cavernosa or crura or the prolongations thereof of the patient's penile tissue;
an implantable adjustment device for adjusting the restriction device to temporarily contract the corpora cavernosa or crura or the prolongations thereof to restrict the blood flow leaving the penis;
an implantable powered, non-manual operation device for operating the adjustment device; and
an energy transmission device for wireless transmission of energy.

86. An apparatus according to claim 85, wherein the energy transmission device transmits energy of a first form, and further comprising an energy transforming device implantable in the patient for transforming the energy of the first form into energy of a second form, to be supplied to the source of energy and/or other implantable energy consuming parts of the apparatus.

87. An apparatus according to claim 86, wherein the energy of the second form is different than the energy of the first form.

88. An apparatus according to claim 86, wherein the energy transmission device functions different from the energy transforming device.

89. An apparatus according to claim 85, further comprising an implantable motor or pump for operating the adjustment device, wherein the energy transmission device is adapted to transmit wireless energy in the form of an magnetic field or electromagnetic waves or field for direct power of the motor or pump, as the wireless energy is being transmitted.

90. An apparatus according to claim 85, wherein the energy transmission device transmits energy by at least one signal separate from the control signal.

91. An apparatus according to claim 86, further comprising an implantable stabiliser for stabilising the energy of the first or second form.

92. An apparatus according to claim 91, wherein the energy of the second form comprises electric current and the stabiliser comprises at least one capacitor.

93. An apparatus according to claim 84, wherein the source of energy comprises a battery, accumulator, capacitor or a combination thereof.

94. An apparatus according to claim 1, further comprising a control device adapted to produce wireless energy for directly powering the operation device and/or for energizing other energy consuming components of the apparatus.

95. An apparatus according to claim 1, further comprising an implantable energy transforming device for transforming wireless energy directly or indirectly into energy different than the wireless energy for operation of the restriction device.

96. An apparatus according to claim 94, wherein the wireless energy comprises a wave signal including a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

97. An apparatus according to claim 1, further comprising an energy transfer means for wireless transfer of energy from outside the patient's body to the operation device or adjustment device and/or other energy consuming implantable components of the apparatus.

98. An apparatus according to claim 94, wherein the control device is adapted to produce wireless energy in the form of a train of energy pulses.

99. An apparatus according to claim 97, wherein the energy transfer means is adapted to intermittently transfer the energy in the form of a train of energy pulses for direct use in connection with the energizing of the energy consuming components of the apparatus.

100. An apparatus according to claim 94 wherein the control device is adapted to control the energy transforming device to produce the energy of the second form in a train of energy pulses for direct use in connection with the operation of the adjustment device.

101. An apparatus according to claim 99, wherein the energy transfer device is adapted to transfer electric energy, and further comprising an implantable capacitor for producing the train of energy pulses.

102. An apparatus according to claim 101, wherein the capacitor has a capacity less than 0.1 µF.

103. An apparatus according to claim 97, further comprising an implantable motor or pump for operating the adjustment device, wherein the energy transfer means is adapted to directly power the motor or pump with transferred energy.

104. An apparatus according to claim 103, wherein the pump is not a plunger type of pump.

105. An apparatus according to claim 1, wherein the adjustment device is adapted to adjust the restriction device in a non-manual, non-thermal or non-magnetic manner.

106. An apparatus according to claim 63, further comprising a wireless remote control for non-invasively controlling the operation device.

107. An apparatus according to claim 1, wherein the operation device is electrically powered.

108. An apparatus according to claim 1, wherein the operation device is unpowerable by static permanent magnetic energy.

109. An apparatus according to claim 1, wherein the operation device is adapted to non-invasively operate the adjustment device.

110. An apparatus according to claim 1, wherein the adjustment device is operable to adjust the restriction device to steplessly change the contraction of the corpora cavernosa or crura or the prolongations thereof.

111. An apparatus according to claim 1, wherein the operation device comprises a hydraulic operation device which uses hydraulic fluid, the viscosity of which changes when the hydraulic fluid is exposed to energy different than thermal energy.

112. An apparatus according to claim 111, wherein the viscosity of the hydraulic fluid changes when the fluid is exposed to electric energy.

113. An apparatus according to claim 1, wherein the adjustment device is adapted to mechanically adjust the restriction device, or adapted to hydraulically adjust the restriction device by using hydraulic means which is devoid of hydraulic fluid of the kind having a viscosity that substantially increases when exposed to heat or a magnetic field.

114. An apparatus according to claim 1, further comprising a control device for controlling the restriction device.

115. An apparatus according to claim 114, wherein the control device comprises an internal control unit implantable in the patient for controlling the restriction device.

116. An apparatus according to claim 115, wherein the internal control unit is programmable.

117. An apparatus according to claim 116, wherein the control device comprises an external control unit outside the patient's body, and wherein the implantable internal control unit is programmable by the external control unit.

118. An apparatus according to claim 114, wherein the control device comprises an external control unit outside the patient's body for wirelessly controlling the restriction device.

119. An apparatus according to claim 118, wherein the external control unit is programmable.

120. An apparatus according to claim 1, further comprising at least one implantable sensor for sensing at least one physical parameter of the patient.

121. An apparatus according to claim 120, wherein the sensor is adapted to directly or indirectly sense as the physical parameter the horizontal position of the patient.

122. An apparatus according to claim 120, wherein the sensor comprises a pressure sensor for directly or indirectly sensing as the physical parameter the pressure against the restriction device or part of the human body.

123. An apparatus according to claim 122, wherein the restriction device is adapted to enlarge the blood flow passageway in the corpora cavernosa or crura or the prolongations thereof in response to the pressure sensor sensing a predetermined pressure.

124. An apparatus according to claim 120, further comprising a control device for controlling the restriction device in response to signals from the sensor.

125. An apparatus according to claim 124, wherein the control device comprises an internal control unit implantable in the patient and directly controlling the restriction device in response to signals from the sensor.

126. An apparatus according to claim 125, wherein the control device comprises an external control unit outside the patient's body for controlling the restriction device in response to signals from the sensor.

127. An apparatus according to claim 125, wherein the control device comprises an external control unit outside the patient's body for manually controlling the restriction device in response to information from the sensor.

128. An apparatus according to claim 114, further comprising an implantable source of energy, wherein the control device is operable from outside the patient's body for controlling the source of energy to release energy for use in connection with the operation of the prosthesis, when the prosthesis is implanted.

129. An apparatus according to claim 128, wherein the source of energy is intended to be external to the patient's body, and the control device is adapted to control the external source of energy to release wireless energy for use in connection with the operation of the prosthesis.

130. An apparatus according to claim 128, wherein the control device controls the source of energy to release magnetic energy, non-magnetic energy, electromagnetic energy, non-electromagnetic energy, kinetic energy, non-kinetic energy, sonic energy, non-sonic energy, thermal energy or non-thermal energy.

131. An apparatus according to claim 1, wherein the operation device is powered by magnetic energy, non-magnetic energy, electromagnetic energy, non-electromagnetic energy, kinetic energy, non-kinetic energy, sonic energy, non-sonic energy, thermal energy or non-thermal energy.

132. An apparatus according to claim 128, wherein the control device controls the source of energy to release energy for a determined time period.

133. An apparatus according to claim 128, wherein the control device controls the source of energy to release energy in a determined number of energy pulses.

134. An apparatus according to claim 128, wherein the control device is adapted to control the source of energy to release energy in a non-invasive manner.

135. An apparatus according to claim 1, further comprising implantable electrical components including at least one voltage level guard.

136. An apparatus according to claim 1, further comprising implantable electrical components including a single voltage level guard.

137. An apparatus according to claim 136, wherein the electrical components are devoid of any current detector and/or charge level detector.

138. An apparatus according to claim 84, further comprising an implantable capacitor or accumulator, wherein the charge or discharge of the capacitor or accumulator is controlled by use of the voltage level guard.

139. An apparatus according to claim 64, wherein the control signal comprises a wave signal including a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

140. An apparatus according to claim 1, further comprising a switch implantable in the patient for directly or indirectly switching the operation of the restriction device.

141. An apparatus according to claim 140, further comprising a source of energy implantable in the patient for supplying energy for the operation of the restriction device, wherein the switch is operated by the energy supplied by the energy transmission device to switch from an off mode, in which the source of energy is not in use, to an on mode, in which the source of energy supplies energy for the operation of the restriction device.

142. An apparatus according to claim 140, further comprising a source of energy implantable in the patient for supplying energy for the operation of the restriction device, and a remote control for controlling the supply of energy of the implantable source of energy, wherein the switch is operated by the energy supplied by the energy transmission device to switch from an off mode, in which the remote control is prevented from controlling the source of energy and the source of energy is not in use, to a standby mode, in which the remote control is permitted to control the source of energy to supply energy for the operation of the restriction device.

143. An apparatus according to claim 140, further comprising a source of energy implantable in the patient for supplying energy for the operation of the restriction device, wherein the switch is operated by the energy supplied by the energy transforming device to switch from an off mode, in which the source of energy is not in use, to an on mode, in which the source of energy supplies energy for the operation of the restriction device.

144. An apparatus according to claim 140, further comprising a source of energy implantable in the patient for supplying energy for the operation of the restriction device, and a remote control for controlling the supply of energy of the implantable source of energy, wherein the switch is operated by the energy supplied by the energy transforming device to switch from an off mode, in which the remote control is prevented from controlling the source of energy and the source of energy is not in use, to a standby mode, in which the remote control is permitted to control the source of energy to supply energy for the operation of the restriction device.

145. An apparatus according to claim 1, wherein the prosthesis is operable to perform a reversible function.

146. An apparatus according to claim 66, further comprising a reversing device implantable in the patient for reversing the function performed by the prosthesis.

147. An apparatus according to claim 146, wherein the control device controls the reversing device to reverse the function performed by the prosthesis.

148. An apparatus according to claim 146, wherein the reversing device comprises hydraulic means including a valve for shifting the flow direction of a flowing fluid in the hydraulic means.

149. An apparatus according to claim 146, wherein the reversing device comprises a mechanical reversing device.

150. An apparatus according to claim 146, wherein the reversing device comprises a switch.

151. An apparatus according to claim 150, wherein the switch of the reversing device is operable by the released energy.

152. An apparatus according to claim 151, wherein the control device controls the operation of the switch of the reversing device by shifting polarity of the released energy supplied to the switch.

153. An apparatus according to claim 146, wherein the operation device comprises a motor, and the reversing device reverses the motor.

154. An apparatus according to claim 1, wherein the restriction device is embedded in a soft or gel-like material.

155. An apparatus according to claim 154, wherein the restriction device is embedded in a silicone material having hardness less than 20 Shore.

156. An apparatus according to claim 86, wherein the energy transforming means or device is designed to be implanted subcutaneously or in the abdomen, thorax or cephalic region of the patient.

157. An apparatus according to claim 124, wherein the restriction device is adapted to release the corpora cavernosa or crura or the prolongations thereof in response to the sensor sensing ejaculation.

158. An apparatus according to claim 1, wherein the restriction device further comprises two restriction members adapted to restrict the respective corpora cavernosa or crura or the prolongations thereof.

159. An apparatus according to claim 1, wherein the restriction device further is adapted to restrict at least one of the penile exit veins.

160. An apparatus according to claim 1, wherein the adjustment device is adapted to adjust the restriction device such that the restriction device provides a predetermined contraction of the corpora cavernosa or crura or the prolongations thereof that is satisfactory for the patient.

161. An apparatus according to claim 1, wherein the adjustment device is adapted to adjust the restriction device in a non-flux magnetic or non-thermal manner or non-viscosity changing manner.

162. A method of treating male sexual impotence, comprising surgically implanting in the patient's body:
    at least one adjustable restriction device engaging the corpora cavernosa or crura or the prolongations thereof of the patient's penile tissue;
    an adjustment device for adjusting the restriction device to temporarily contract the corpora cavernosa or crura or the prolongations thereof to restrict the blood flow leaving the penis;
    powered operation device for operating the adjustment device, and
    a reservoir containing hydraulic fluid,
powering said operation device to operate said adjustment device by distributing fluid from said reservoir, whereby said restriction device is adjusted to temporarily restrict the blood flow leaving the penis to achieve erection.

163. A surgical method according to claim 162, comprising implanting an elongated restriction member of the restriction device around the corpora cavernosa or crura or its prolongation.

164. A surgical method as recited in claim 162, restriction device in the base of the patient's penis or its prolongation.

165. A method according to claim 162, comprising:
    surgically implanting in the body of a male patient suffering from sexual impotence at least two adjustable restriction devices to affect the blood flow leaving the penis engaging respective of the corpus cavernosa or crura of the penis or its prolongation as separate units of the patient's penis, and
    when desired to achieve erection, non-manually without touching the skin of the patient adjusting said powered restriction device to temporarily restrict the corpora cavernosa or crura or its prolongation to restrict the blood flow leaving the penis.

166. A method for treating male sexual impotence, according to claim 164 comprising:
    surgically implanting in the body of a male patient suffering from sexual impotence several non-manually adjusted powered restriction devices engaging respective exit veins from the penis.

167. A method for treating male sexual impotence, comprising the steps of:
    placing at least two laparascopical trocars in the body of a male patient suffering from sexual impotence,
    inserting a dissecting tool through the trocars and dissecting an area of the penis and abdominal or retroperitoneal or pelvic surroundings,
    placing at least one adjustable restriction device in the dissected area engaging the penile tissue or the prolongation thereof, further placing in the dissected area:
- an adjustment device for adjusting the restriction device
- a powered operation device for operating the adjustment device, and
- a resevoir containing hydraulic fluid; and powering said operation device to operate said adjustment device by distributing fluid from said reservoir, whereby said restriction device is adjusted to temporarily restrict the blood flow leaving the penis to achieve erection.

168. A surgical method as recited in claim 167, further comprising hydraulically adjusting said restriction device.

169. A surgical method as recited in claim 167, wherein the restriction device engages both of the corpus cavernosa or crura of the penis or the prolongations thereof as a single unit.

170. A surgical method as recited in claim 167, further comprising implanting a further adjustable restriction device, wherein the two restriction devices engage the two corpus cavernosa or crura of the penis or their prolongations, respectively, as separate units.

171. A surgical method as recited in claim 167, wherein the restriction device engages one of the exit veins from the penis.

172. A surgical method as recited in claim 167, further comprising implanting several restriction devices engaging respective exit veins from the penis.

173. A surgical method as recited in claim 167, further comprising implanting a source of energy in the patient and providing a control device for controlling the source of energy from outside the patient's body to supply energy to the operation device.

174. A surgical method as recited in claim 173, further supplying said source of energy with wirelessly transmitted energy from outside the patient's body.

* * * * *